United States Patent
Escalona et al.

(10) Patent No.: US 11,191,973 B2
(45) Date of Patent: Dec. 7, 2021

(54) TRANSCUTANEOUS ENERGY TRANSFER SYSTEMS AND METHODS

(71) Applicant: University of Ulster, Coleraine (GB)

(72) Inventors: Omar Jacinto Escalona, Carrickfergus (GB); David John McEneaney, Belfast (GB); James McLaughlin, Belfast (GB)

(73) Assignee: University of Ulster, Northern Ireland (GB)

( * ) Notice: Subject to any disclaimer, the term of this patent is extended or adjusted under 35 U.S.C. 154(b) by 0 days.

(21) Appl. No.: 15/748,894

(22) PCT Filed: Jul. 29, 2016

(86) PCT No.: PCT/IB2016/054555
§ 371 (c)(1),
(2) Date: Jan. 30, 2018

(87) PCT Pub. No.: WO2017/021846
PCT Pub. Date: Feb. 9, 2017

(65) Prior Publication Data
US 2018/0280708 A1 Oct. 4, 2018

(30) Foreign Application Priority Data
Jul. 31, 2015 (GB) .................... 1513596

(51) Int. Cl.
*A61N 1/39* (2006.01)
*A61N 1/378* (2006.01)
(Continued)

(52) U.S. Cl.
CPC ......... *A61N 1/3975* (2013.01); *A61M 60/148* (2021.01); *A61N 1/3787* (2013.01);
(Continued)

(58) Field of Classification Search
CPC .... A61N 1/3787; A61N 1/36125; A61N 1/40; A61N 1/375; A61N 1/0472; A61N 1/36;
(Continued)

(56) References Cited

U.S. PATENT DOCUMENTS

| 4,918,745 A | 4/1990 | Hutchison |
| 6,430,444 B1 | 8/2002 | Borza |

(Continued)

FOREIGN PATENT DOCUMENTS

| EP | 0247649 | 12/1987 |
| EP | 2289596 | 3/2011 |

(Continued)

OTHER PUBLICATIONS

Bossetti, Chad. "Design and evaluation of a transcutaneous energy transfer system." PhD diss., Duke University, 2009.
(Continued)

*Primary Examiner* — Deborah L Malamud
(74) *Attorney, Agent, or Firm* — Diederiks & Whitelaw, PLC

(57) ABSTRACT

An external transmitter apparatus for a transcutaneous energy transfer (TET) system for supplying power for use in energising an implantable medical device is disclosed, the apparatus comprising an external transmitter apparatus comprising a plurality of transmitter coils for delivering power transcutaneously to one of a plurality of receiver coils of an implantable receiver apparatus of the TET system when located in proximity thereto. The external transmitter apparatus is provided with power by a pulsed power supply. The coils of the external transmitter apparatus and the implantable receiver apparatus may be printed on flexible substrates. Also disclosed are methods of operating such a system, an external transmitter apparatus for use in such a system, an
(Continued)

external transmitter apparatus and an implantable receiver apparatus including flexible coils.

21 Claims, 13 Drawing Sheets

(51) Int. Cl.

| | | |
|---|---|---|
| *A61M 60/148* | (2021.01) | |
| *H02J 50/10* | (2016.01) | |
| *H02J 50/40* | (2016.01) | |
| *H01F 27/28* | (2006.01) | |
| *H02J 7/02* | (2016.01) | |
| *H02J 7/34* | (2006.01) | |

(52) U.S. Cl.
CPC ........ *A61N 1/3956* (2013.01); *H01F 27/2804* (2013.01); *H02J 7/025* (2013.01); *H02J 50/10* (2016.02); *H02J 50/40* (2016.02); *A61M 2205/8206* (2013.01); *A61M 2205/8243* (2013.01); *A61M 2209/088* (2013.01); *A61M 2230/50* (2013.01); *H02J 7/345* (2013.01)

(58) Field of Classification Search
CPC ... A61N 1/00; A61N 1/05; A61N 1/08; A61N 1/3975; H02J 7/025; H02J 50/10; H02J 50/40; A61B 5/0031; A61B 5/4836; A61B 2560/0219; A61B 5/6801
See application file for complete search history.

(56) References Cited

U.S. PATENT DOCUMENTS

| | | | |
|---|---|---|---|
| 6,516,227 B1* | 2/2003 | Meadows | A61N 1/36071 |
| | | | 607/46 |
| 8,014,865 B2 | 9/2011 | Najafi et al. | |
| 8,229,567 B2 | 7/2012 | Phillips et al. | |
| 8,412,332 B2 | 4/2013 | Massoud-Ansari et al. | |
| 8,738,139 B2* | 5/2014 | Lanning | A61B 5/6814 |
| | | | 607/45 |
| 8,862,241 B2 | 10/2014 | Forsell | |
| 9,259,583 B2 | 2/2016 | Forsell | |
| 9,393,428 B2 | 7/2016 | Nyberg, II et al. | |
| 9,653,935 B2 | 5/2017 | Cong et al. | |
| 9,737,707 B2 | 8/2017 | Haessler et al. | |
| 2009/0204173 A1 | 8/2009 | Fang et al. | |
| 2009/0276016 A1 | 11/2009 | Philips et al. | |
| 2011/0218383 A1 | 9/2011 | Broen et al. | |
| 2012/0119700 A1* | 5/2012 | Forsell | A61N 1/37229 |
| | | | 320/108 |
| 2012/0157753 A1 | 6/2012 | D'Ambrosio | |

FOREIGN PATENT DOCUMENTS

| | | |
|---|---|---|
| WO | 2012/047967 | 4/2012 |
| WO | 2012/087807 | 6/2012 |

OTHER PUBLICATIONS

Dearden et al. "A Low Curing Temperature Silver Ink for Use in Ink-Jet Printing and Subsequent Production of Conductive Tracks." *Macromolecular Rapid Communications* 26, No. 4 (2005): 315-318.
Dissanayake et al. "A novel low temperature transcutaneous energy transfer system suitable for high power implantable medical devices: performance and validation in sheep." Artificial organs 34, No. 5 (2010), E160-E167.
Escalona et al. "Transcutaneous dual tuned RF coil system voltage gain and efficiency evaluation for a passive implantable atrial defibrillator." In Computing in Cardiology, 2010, IEEE, 2010, pp. 569-572.
Leung et al. "Minimizing power loss in air-cored coils for TET heart pump systems." *IEEE journal on emerging and selected topics in circuits and systems* 1, No. 3 (2011): 412-419.
Mager et al. "An MRI receiver coil produced by inkjet printing directly on to a flexible substrate." *IEEE transactions on medical imaging* 29, No. 2 (2010): 482-487.
Manoharan et al. "Novel passive implantable atrial defibrillator using transcutaneous radiofrequency energy transmission successfully cardioverts atrial fibrillation." *Circulation* 108, No. 11 (2003): 1382-1388.
Slaughter et al. "Transcutaneous energy transmission for mechanical circulatory support systems: history, current status, and future prospects." *Journal of cardiac surgery* 25, No. 4 (2010): 484-489.
Stewart et al. "Keeping Left Ventricular Assist Device Acceleration on TrackResponse to Stewart and Stevenson." *Circulation* 123, No. 14 (2011): 1559-1568.
Stieglitz et al. "Evaluation of polyimide as substrate material for electrodes to interface the peripheral nervous system." In *Neural Engineering (NER)*, 2011 5th *International IEEE/EMBS Conference on*, IEEE, 2011, pp. 529-533.

* cited by examiner (14 V)

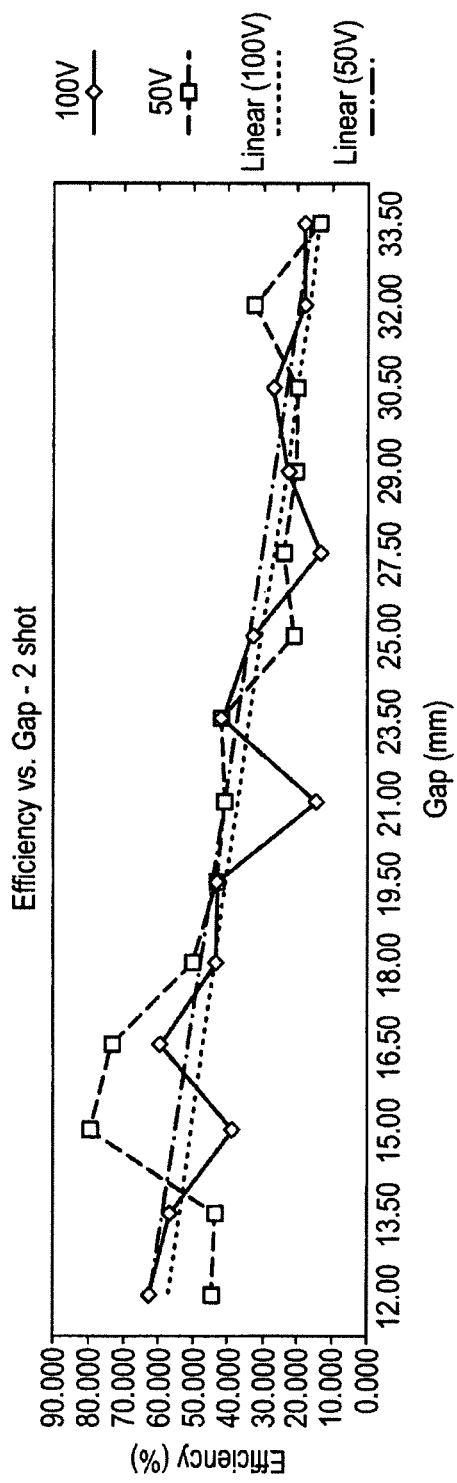

TRANSCUTANEOUS ENERGY TRANSFER SYSTEMS AND METHODS

CROSS-REFERENCE TO RELATED APPLICATIONS

This application represents the U.S. National Phase of International Application number PCT/IB2016/054555 entitled "Transcutaneous Energy Transfer Systems and Methods" filed 29 Jul. 2016, which claims priority from and the benefit of United Kingdom patent application No. 1513596.5 filed on 31 Jul. 2015.

The present invention relates to an external transmitter apparatus for a transcutaneous energy transfer (TET) system for supplying power for use in energising an implantable medical device in use, and a method of operating the same. The present invention also relates to a transcutaneous energy transfer system including the external transmitter apparatus and an implantable receiver apparatus, and a method for operating the same. Further aspects of the invention relate to the implantable receiver apparatus for a TET system, and methods of operating the same. In accordance with some further aspects the present invention relates to a coil construction for a transmitter or receiver coil, and methods for manufacturing such a coil.

BACKGROUND OF THE INVENTION

Transcutaneous energy transfer (TET) systems are increasingly used to supply power to implantable medical devices. These enable power to be supplied to an implanted medical device from outside the body across the skin interface. This is typically achieved using an external transmitter apparatus including a transmitter coil, which is able to transmit power transcutaneously to a receiver coil of an implanted receiver apparatus connected to the implantable device in use. Power may be transmitted between the transmitter coil and the receiver coil by electromagnetic induction. For example, the external transmitter coil may be arranged to inductively couple to the internal receiver coil, and an alternating current applied to the transmitter coil used to induce an alternating current in the receiver coil, which may then be rectified and processed as required to power the implantable device. TET systems are advantageous as, in contrast to percutaneous energy transfer systems, the need to pierce the skin is avoided. This may reduce the risk of infection, and allows the system to be installed using a less invasive process.

However, existing TET systems for implantable medical devices suffer from some limitations. Many implantable medical devices now require the continuous supply of energy at relatively high power levels, e.g. greater than 2 W. Further energy may be required in order to recharge an implanted back up power source e.g. battery for some types of device. The use of such higher power rated implantable medical devices is increasing. Examples of such devices include artificial heart pumps e.g. ventricular assist devices (VADs) and total artificial hearts (TAHs). Conventional TET systems suffer from the disadvantage that, when used to deliver higher levels of power, there may be undesirable excessive heating of the skin. The systems may also be relatively inefficient in transferring energy at higher power levels.

SUMMARY OF THE INVENTION

In accordance with a first aspect, the present invention seeks to provide an improved external apparatus for a TET system, which may, in preferred embodiments at least, overcome some of these problems.

In accordance with a first aspect of the invention there is provided an external transmitter apparatus for a transcutaneous energy transfer (TET) system for supplying power for use in energising an implantable medical device in use, the external transmitter apparatus comprising;

a plurality of transmitter coils, each transmitter coil being capable of transmitting power transcutaneously to a respective one of a plurality of receiver coils of an implantable receiver apparatus of the TET system when located in proximity thereto in use for use in energising an implantable medical device connected to the implantable receiver apparatus in use, the external transmitter apparatus for the TET further comprising power supply means for providing a pulsed power supply to each one of the transmitter coils of the external transmitter apparatus in use for transmission transcutaneously by the transmitter coil to a respective receiver coil of the implantable receiver apparatus when located in proximity thereto, wherein each transmitter coil is associated with a respective power supply channel, and the power supply means is arranged to deliver the pulsed power supply to each transmitter coil over the respective power supply channel associated therewith.

In accordance with the invention, the external transmitter apparatus for the TET system is arranged to be able to supply power for use in energising an implantable receiver apparatus of the TET system via a plurality of transmitter coils. The invention in the first aspect relates to the external transmitter apparatus per se. Each transmitter coil of the external apparatus is arranged to transmit power to a respective one of a plurality of receiver coils of the implantable apparatus when located in proximity thereto in use. Each transmitter coil will then define a transmitter-receiver coil pair with the respective receiver coil. A power supply means of the external apparatus is arranged to provide a pulsed power supply to each of the plurality of transmitter coils of the external transmitter apparatus. Each coil is associated with a respective power supply channel, and the power supply means is operable to deliver pulsed power to each coil over its respective power supply channel.

It will be appreciated that the external transmitter apparatus for the TET system to which the present invention is directed in its various aspects or embodiments is arranged to supply power wirelessly to an implantable receiver apparatus of the TET system, for use in energising an implantable medical device connected to the implantable receiver apparatus in use. The external apparatus is arranged such that power may be transmitted from each one of the transmitter coils of the external apparatus through the skin of a user in use to a respective one of a plurality of receiver coils of an implantable receiver apparatus of the TET system located in proximity thereto. Each one of the transmitter coils is arranged to be able to inductively couple to a respective one of the receiver coils of the implantable device when located in proximity thereto. It will be appreciated that power supplied by a transmitter coil of the external apparatus is for use in supplying power to i.e. energising the implantable medical device. As discussed below, the power may be used directly to power/energise the device, or may be used to power/energise a rechargeable backup battery associated with the device, where provided. References herein to the TET system or external apparatus thereof providing power for use in supplying power to an implantable medical device may be used interchangeably with references to providing power for use in energising the device.

Thus, the external transmitter apparatus of the present invention delivers power to the implantable receiver apparatus of the TET system for use in energising an implantable medical device connected to the receiver apparatus over multiple channels associated with different ones of a plurality of transmitter coils of the external apparatus, and hence with different ones of a plurality of receiver coils of the implantable medical device. Furthermore, the power supplied to each transmitter coil is a pulsed power supply. These features help to overcome the problem of skin overheating, which is often associated with conventional TET systems, which supply power to an implantable medical device continuously over a single channel. As multiple power supply channels are present in accordance with the invention, one for each coil, power may be supplied to different ones of the transmitter coils at different times, spreading the heating effect over a greater area, as the transmitter coils may be associated with different portions of skin. In some embodiments, if a particular portion of the skin associated with one of the transmitter coils is found to be becoming undesirably hot, then the channel associated with that coil may be temporarily disabled, or a rate of delivery of pulses over the channel decreased. The use of multiple channels provides greater flexibility in general. For example, a dedicated channel may be used for recharging a backup battery associated with the implantable device, where such a battery is provided. In addition, the use of a pulsed rather than continuous power supply further helps to reduce skin heating, reducing the time over which power is delivered, with the skin temperature able to recover during the intervals between pulses.

The term "transmitter coil" in accordance with the invention in any of its aspects or embodiments relating to a TET system, or external transmitter or implantable receiver apparatus therefor, refers to a coil which is arranged to perform a transmitting function. The coil may be arranged only to transmit, or may be arranged to both receive and transmit. Preferably the coil is arranged solely to transmit. The term "receiver coil" in accordance with any of its aspects or embodiments relating to a TET system, or external transmitter or implantable receiver apparatus therefor, refers to a coil which is arranged to perform a receiving function. The coil may be arranged only to receive, or may be arranged to both receive and transmit. Preferably the coil is arranged solely to receive.

The present invention extends to a transcutaneous energy transfer (TET) system comprising the external transmitter apparatus of the invention in accordance with any of its aspects and embodiments and an implantable apparatus of the TET system, wherein the implantable apparatus is connected or connectable to an implantable medical device for energising the device i.e. supplying power thereto.

The present invention extends to a transcutaneous energy transfer (TET) system for supplying power for use in energising an implantable medical device in use, the TET system comprising;

an external transmitter apparatus and an implantable receiver apparatus, wherein the implantable receiver apparatus is connected or connectable to an implantable medical device for supplying power thereto in use;

the external transmitter apparatus comprising a plurality of transmitter coils, each transmitter coil being capable of transmitting power transcutaneously to a respective one of a plurality of receiver coils of the implantable receiver apparatus when located in proximity thereto in use for use in energising an implantable medical device connected to the implantable receiver apparatus in use, the external transmitter apparatus of the TET system further comprising power supply means for providing a pulsed power supply to each one of the transmitter coils of the external transmitter apparatus in use for transmission transcutaneously by the transmitter coil to a respective receiver coil of the implantable receiver apparatus when located in proximity thereto, wherein each transmitter coil is associated with a respective power supply channel, and the power supply means is arranged to be able to deliver the pulsed power supply to the transmitter coil over the respective power supply channel associated therewith.

It will be appreciated that the present invention in accordance with the further aspect may include any or all of the features described in relation to any of the embodiments of the earlier aspects of the invention to the extent they are not mutually inconsistent therewith, and vice versa.

Each one of the transmitter coils of the external transmitter apparatus defines a transmitter-receiver coil pair in use with the respective one of the plurality of receiver coils of the implantable receiver apparatus in proximity thereto for transcutaneously transmitting power thereto. The transmitter coils of the external transmitter apparatus and the receiver coils of the implantable receiver apparatus thus define a plurality of transmitter-receiver coil pairs. Each transmitter coil is associated with a single receiver coil for transmitting power thereto. In use, each transmitter coil is associated with a different respective one of the plurality of receiver coils for transmitting power thereto.

The transmitter and receiver coils of a given transmitter-receiver coil pair will both be associated with the power supply channel associated with the transmitter coil. The transmitter and receiver coil of each coil pair face one another on opposite sides of the skin interface in use. Each transmitter coil of the external transmitter apparatus of the TET system is arranged to wirelessly transmit power transcutaneously to the respective receiver coil of the implantable apparatus. Thus transmission of power between the transmitter and receiver coil of a respective transmitter-receiver coil pair is wireless.

The present invention extends to a method of operating the external apparatus for a TET system in accordance with the earlier aspect of the invention in any of its embodiments to deliver power to at least some of a plurality of receiver coils of an implantable apparatus of the TET system for use in energising an implantable medical device connected to the implantable apparatus, the method comprising using the power supply means of the external apparatus to provide a pulsed power supply to each one of the at least some of the plurality of transmitter coils of the external transmitter apparatus over the respective power supply channel associated with the coil.

The present invention also extends to a method of operating the TET system in accordance with the earlier aspect of the invention in any of its embodiments for supplying power for use in energising an implantable medical device connected to the implantable apparatus. The method in accordance with this further aspect in any of its embodiments may comprise using the power supply means to provide a pulsed power supply to each one of at least some of the plurality of coils of the external transmitter apparatus over the respective power supply channel associated with the coil.

It will be appreciated that the present invention in accordance with the further aspects may include any or all of the features described in relation to any of the embodiments of the earlier aspects of the invention to the extent they are not mutually inconsistent therewith, and vice versa.

In accordance with a further aspect of the invention there is provided a method of operating an external transmitter apparatus for a transcutaneous energy transfer (TET) system for supplying power for use in energising an implantable medical device in use, the external transmitter apparatus comprising;

a plurality of transmitter coils, each transmitter coil being capable of transmitting power transcutaneously to a respective one of a plurality of receiver coils of an implantable receiver apparatus of the TET system when located in proximity thereto in use for use in supplying power to an implantable medical device connected to the implantable receiver apparatus in use, the external transmitter apparatus for the TET system further comprising power supply means for providing a pulsed power supply to each one of the transmitter coils of the external transmitter apparatus in use for transmission transcutaneously by the transmitter coil to a respective receiver coil of the implantable receiver apparatus located in proximity thereto, wherein each transmitter coil is associated with a respective power supply channel, and the power supply means is arranged to deliver the pulsed power supply to each transmitter coil over the respective power supply channel associated therewith, the method comprising using the power supply means to provide a pulsed power supply to each one of at least some of the plurality of transmitter coils of the external transmitter apparatus in use over the respective power supply channel associated with the coil.

It will be appreciated that the present invention in accordance with the further aspect may include any or all of the features described in relation to any of the embodiments of the earlier aspects of the invention to the extent they are not mutually inconsistent therewith, and vice versa.

In accordance with yet another aspect of the invention there is provided a method of operating a transcutaneous energy transfer (TET) system to supply power for use in energising an implantable medical device in use, the TET system comprising;

an external transmitter apparatus and an implantable receiver apparatus, wherein the implantable receiver apparatus is connected to an implantable medical device for supplying power thereto, the external transmitter apparatus of the TET system comprising a plurality of transmitter coils, each transmitter coil being capable of transmitting power transcutaneously to a respective one of a plurality of receiver coils of the implantable receiver apparatus of the TET system when located in proximity thereto in use for use in supplying power to an implantable medical device connected to the implantable receiver apparatus in use, the external transmitter apparatus of the TET system further comprising power supply means for providing a pulsed power supply to each one of the transmitter coils of the external transmitter apparatus in use for transmission transcutaneously by the transmitter coil to a respective receiver coil of the implantable receiver apparatus located in proximity thereto, wherein each transmitter coil is associated with a respective power supply channel, and the power supply means is arranged to deliver the pulsed power supply to each transmitter coil over the respective power supply channel associated therewith, the method comprising using the power supply means to provide a pulsed power supply to each one of at least some of the plurality of transmitter coils of the external transmitter apparatus in use over the respective power supply channel associated with the transmitter coil for transmission to the respective one of the receiver coils of the implantable receiver apparatus located in proximity thereto.

It will be appreciated that the present invention in accordance with the further aspect may include any or all of the features described in relation to any of the embodiments of the earlier aspects of the invention to the extent they are not mutually inconsistent therewith, and vice versa.

In these further aspects and embodiments of the invention relating to the use of the external transmitter apparatus, or the TET system, a pulsed power supply is provided to at least some of the transmitter coils, and preferably to a plurality, or to each of the transmitter coils. The power supply is provided over those active power supply channel(s) i.e. to active transmitter coil(s). The power may therefore be transmitted transcutaneously to at least some, and preferably to a plurality or to each one of the receiver coils of the implantable apparatus.

The present invention also extends to an implantable receiver apparatus for a TET system connected or connectable to an implantable medical device for use with the external transmitter apparatus for the TET system in accordance with any of its aspects or embodiments. The implantable receiver apparatus of the TET system comprises a plurality of receiver coils, each receiver coil being arranged to receive a pulsed power supply from a respective one of the plurality of transmitter coils of the external transmitter apparatus for the TET system when in proximity thereto.

It will be appreciated that the present invention in accordance with the further aspect may include any or all of the features described in relation to any of the embodiments of the earlier aspects of the invention to the extent they are not mutually inconsistent therewith, and vice versa.

In any of the aspects or embodiments of the invention relating to the implantable receiver apparatus, whether forming part of the TET system or not, the apparatus is connected or connectable to an implantable medical device. Preferably the implantable receiver apparatus is connected to the implantable medical device. Where the apparatus is connected to the device, the implantable receiver apparatus may be integral with the medical device, or may be attached to a separate medical device e.g. removably connected thereto.

In any of the aspects or embodiments of the invention relating to or including the implantable receiver apparatus, each receiver coil of the apparatus is arranged to receive power from the external transmitter apparatus from a respective transmitter coil thereof over a respective power supply channel associated with the transmitter coil. Each receiver coil of the implantable receiver apparatus is therefore effectively associated with a respective power receiving channel of the implantable apparatus.

The present invention also extends to a method of operating an implantable apparatus of a TET system connected or connectable to an implantable medical device for use with the external transmitter apparatus of the TET system in accordance with any of its aspects or embodiments. The implantable apparatus of the TET system comprises a plurality of receiver coils, and the method comprises each one of at least some (e.g. one or more, a plurality, or each) of the receiver coils receiving a pulsed power supply from a respective one of the plurality of transmitter coils of the external transmitter apparatus of the TET system when in proximity thereto.

It will be appreciated that any of the features described in relation to the external transmitter apparatus for the TET system are applicable to those aspects of the invention relating to the external transmitter apparatus, or to the TET system including the external transmitter apparatus. Likewise, any of the features described in relation to the use of the external transmitter apparatus for the TET system are applicable to those aspects of the invention relating to the use of the TET system including the external transmitter apparatus. Features described herein relating to the implantable receiver apparatus of the TET system, or the implantable device, are applicable to any of the aspects of the invention referring to the implantable receiver apparatus or implantable device, whether directed to the implantable receiver apparatus per se, its use, or a TET system including the external transmitter apparatus and the implantable receiver apparatus.

The present invention extends to an external transmitter apparatus for the TET system arranged to perform any of the functions the external transmitter apparatus is described as performing in the context of the overall TET system, and to an implantable receiver apparatus for the TET system arranged to perform any of the functions the implantable receiver apparatus is described as performing in the context of the overall TET system. The invention extends to a TET system in which the external transmitter apparatus or the implantable receiver apparatus is arranged to perform any of the functions described in relation to the external transmitter apparatus or the implantable receiver apparatus per se.

The invention extends to the TET system or an implantable receiver apparatus for a TET system in which the implantable receiver apparatus is implanted in the body of a user i.e. in which the system or receiver apparatus is in situ. The receiver coils of the implantable medical device are located at different locations within the body. The receiver coils of the implantable medical device are arranged to receive power from the transmitter coils of the external apparatus transcutaneously i.e. through the skin of the user. The receiver coils are typically provided on the interior of the skin interface. For example, at least some of the coils may be adhered to the interior of the chest wall. The locations are separate areas. For example, for cardiac applications, the locations may include the waist and upper left and right chest wall. In some embodiments at least some of the coils may alternatively or additionally be adhered to the interior of a wall of the abdomen of a user. For example, a pair of coils may be adhered to the interior of the chest wall, and a pair to the interior of the abdomen of a user. The method of operating the TET system or implantable apparatus may extend to implanting the implantable receiver apparatus in the body of a user, with the receiver coils located in any of the manners described above.

The external transmitter apparatus for the TET system remains outside the body of a user when the TET system is installed in use. All components of the external transmitter apparatus are located outside the body of the user i.e. outside the skin interface. There is no percutaneous connection between the external transmitter apparatus and the implantable receiver apparatus of the TET system. The implantable receiver apparatus i.e. internal apparatus of the TET system is located within the body of the user when the TET system is installed in use. All components of the implantable receiver apparatus are located within the body of the user i.e. inside the skin interface. It will be appreciated that the implantable receiver apparatus of the TET system may be arranged to be located within the body for an extended period of time, or only temporarily, such as during a surgical or diagnostic procedure.

Each transmitter coil of the external transmitter apparatus may be releasably attached to a part of the external transmitter apparatus to permit power to be supplied thereto e.g. to the power supply means thereof. This may permit coils to be replaced if desired e.g. when attached to a garment providing a disposable coil unit.

The external transmitter apparatus of the TET system may comprise means for locating the external transmitter apparatus with respect to the body of a user in use. The external transmitter apparatus may be adapted to be worn by a user. For example, at least a part of the external transmitter apparatus may be connected to a belt and/or garment such as a vest or short which may be worn by the user. The power supply means e.g. a power source and circuitry associated with the power supply means may be mounted to the belt. As described below, at least a part of the external transmitter apparatus e.g. the transmitter coils thereof may be mounted to one or more wearable garments e.g. a vest or shorts. In embodiments, the transmitter coils of the transmitter apparatus are mounted to one or more garments which are worn by the user. Each such garment may provide a coil unit for the external transmitter apparatus. The external transmitter apparatus is typically arranged to be removably worn by a wearer in use. The user may then remove the apparatus e.g. when washing.

Each transmitter coil of the external transmitter apparatus is preferably locatable in a different position with respect to the body of the wearer, and is preferably independently locatable. This enables the coils to be associated with i.e. located in proximity to different portions of the body of the wearer in use, each in proximity to a given receiver coil of the implantable receiver apparatus. Each transmitter coil is therefore preferably locatable in proximity to the body of the wearer in a respective one of a plurality of different locations in use. Each transmitter coil, and hence power supply channel, of the external transmitter apparatus may be associated with a particular anatomical location in use. Each transmitter coil may be locatable in a respective different one of two or more of the following locations of the body; the waist, the upper left chest wall, and the upper right chest wall. Other locations may include locations on the abdomen. For example a pair of transmitter coils may be locatable on the chest of a user and a pair of transmitter coils to an abdomen of the user. Each transmitter coil may be associated with means for mounting the coil to the body of a wearer in proximity to a respective receiver coil of an implantable apparatus of the TET system in use. The mounting is typically a releasable mounting. The mounting means may directly or indirectly mount the coil to the body of the wearer. For example, each transmitter coil may comprise means for adhesively mounting the coil to the body (e.g. skin) or a garment. While a transmitter coil may directly contact the skin of a user in its respective location, and in some embodiments does so, this need not be the case. A transmitter coil may instead be mounted to e.g. attached to a garment which is worn by a user to locate the coil in its respective location in proximity to the body. Thus, the transmitter coils may be provided as part of a wearable garment or garments and thus held in proximity to the body of a wearer. The coils may be permanently or releaseably attached to the garment(s). The or a wearable garment may be a vest. In some embodiments some of the transmitter coils are mounted to a vest and some to a short type garment. Of course, where the coil does not directly contact the skin of the wearer, it should be ensured that the coil is mounted in proximity to the skin such that the resulting interface between the coil and a receiver coil of the implantable receiver apparatus permits transmission of power transcutaneously to the receiver coil of the receiver apparatus. Mounting transmitter coils to a wearable garment may help to ensure that the coils are located appropriately with respect to the body of the wearer, and permit the coils to be removed from the body of the wearer e.g. to allow the user to wash, and subsequently replaced with reliable positioning.

In accordance with the invention, transmitter coils of the external transmitter apparatus of any of its aspects or embodiments may therefore be mounted to one or more wearable garment, such as vest or shorts. Each coil is mounted to a given one of the wearable garments where multiple garments are provided. The one or more garment preferably includes a garment that is adapted to be worn about chest and/or abdomen of the wearer. The or each garment may include at least a pair of transmitter coils. Each garment provides a coil unit for the apparatus. The or each garment may be a flexible garment e.g. woven or nonwoven garment. The garment may be disposable i.e. not intended to be washed. The or each garment may be a garment that is intended to contact the skin of the wearer in use, or may be worn over a user's conventional underwear. The coils are mounted to the exterior i.e. non skin facing side thereof. The transmitter coils may all be mounted to the same garment, or some may be mounted to one garment e.g. a vest and some to another garment e.g. shorts. The invention extends to a wearable garment having at least some of the coils of the external transmitter apparatus mounted thereto. It will be appreciated that other parts of the external transmitter apparatus may be mounted to the wearable garment or to separate means for mounting to the body of the wearer, such as a belt. Where the or each garment is disposable, the transmitter coils may be arranged to be releaseably connected to a part of a remainder of the external apparatus e.g. using suitable connectors such as wires, to enable the coil unit i.e. the garment and its coils to be replaced by a new coil unit i.e. a new garment or garments having one or more coils. The part of the remainder of the apparatus permits the power supply to be provided to the coil e.g. comprises the power supply means, and may be provided on a belt. It is envisaged that some transmitter coil(s) may be provided on a wearable garment, and others not provided on a wearable garment so as to be secured directly to the body of the wearer, although in other embodiments all transmitter coils are provided on a wearable garment.

The method of operating the TET system or external transmitter apparatus may extend to locating the transmitter coils of the external transmitter apparatus with respect to the body of a user in any of the manners described above.

It will be appreciated that in accordance with the invention in any of its aspect or embodiments, each of the power supply channels of the external transmitter apparatus will be associated with a different area of the body of the user in use, being the area at which the transmitter coil associated with the power supply channel is located for transmitting power transcutaneously to the respective one of the receiver coils of the implantable medical device associated with the transmitter coil i.e. with which it defines a transmitter-receiver coil pair. The area of the body will correspond to the location of the respective receiver coil to which the transmitter coil transmits power. In cardiac applications, the areas of body may therefore include areas in the waist, and upper left and right chest wall of the user. Alternatively or additionally, including in cardiac applications, the areas of the body may include one or more areas e.g. at least a pair of areas in the abdomen of the user. The power supply means of the external apparatus comprises a power source, such as a battery. The power source may be a rechargeable power source e.g. battery. In some exemplary embodiments the power source is a lithium ion rechargeable battery. It will be appreciated that the power supply means (and power source) are located external to the body in use. The power supply means preferably further comprises energy storage means. The energy storage means temporarily stores energy from the power source for use in providing the pulsed power supply on each of the plurality of power supply channels. The energy storage means preferably comprises a capacitor arrangement. The capacitor arrangement may then comprise one or more capacitors. The energy storage means may comprise individual energy storage means in respect of each power supply channel e.g. a plurality of capacitor arrangements, each being dedicated to a given power supply channel. However, preferably a common energy storage means is provided that is shared by at least some channels, or preferably each channel e.g. a single capacitor arrangement. This may provide a less bulky arrangement.

The power supply means further comprises means for generating a pulsed power supply for provision on each of the channels. The pulsed power supply generating means is capable of providing a pulsed power supply on each of the channels, although, as described below, in practice, a pulsed power supply may not always be supplied over each of the different channels e.g. one or more channel may be temporarily disabled. A pulsed power supply may be provided on a subset of e.g. at least one, or a plurality, or each of the channels which is/are active. The pulsed power supply is generated using energy provided by the power source of the power supply means, and, in embodiments, which is subsequently stored by an energy storage means of the power supply means prior to use in generating the pulsed power supply. The generating means may comprise any suitable circuitry. In preferred embodiments the generating means comprises one or more switching arrangement for use in generating a pulsed power supply on each channel. A switching arrangement may be provided in respect of each channel. Alternatively a common switching arrangement may be associated with more than one, or each channel. This may provide a less bulky arrangement. Thus one or more switching arrangements may be provided. Where a single switching arrangement is associated with multiple channels, the generating means may comprise channel selector means to select the channel or channels on which a pulse is to be provided at any time. In each switching arrangement, the switch may be alternately switched on and off to provide pulses on the or a channel. Thus, the switch may generate a pulse corresponding to the duration that the switch is "on". The or each switching arrangement may comprise a switching transistor e.g. an RF power switching transistor. However it is generated, the pulsed power supply is of a suitable form that may be used by the transmitter coil associated with the channel to transmit power to a receiver coil of the implantable receiver apparatus when located in proximity thereto. The pulsed power supply provided on each channel comprises a series of discrete pulses. The pulses are separated by intervals in which no power is delivered on the channel.

It will be appreciated that the construction of the power supply means may vary provided that the required pulsed power supply may be provided on each channel as required. For example, each channel may have its own energy storage means and switching means, or the same energy storage means and/or switching means may be common to multiple ones of, or each channel.

Each of the power supply channels may be of any suitable type, enabling a pulsed power supply to be delivered over the channel by the power supply means to the respective transmitter coil associated with the channel. Each channel connects the power supply means to a given one of the plurality of transmitter coils. Each channel is dedicated to a particular transmitter coil. One power supply channel is provided in respect of each transmitter coil. The same channel remains associated with the same transmitter coil. The channels are independent channels, wherein power may be supplied over any one of the channels independently of any other one of the channels. This enables pulses to be supplied to any one or ones of the transmitter coils independently of the other ones of the transmitter coils i.e. at different times. The rate of pulses supplied and/or other parameters e.g. relating to the pulses supplied may be set differently on different ones of the channels, and may vary over time on a particular channel. Furthermore, power may be delivered over one channel and not another. However, it will be appreciated that the pulsed power supplied on each given channel e.g. the rate and/or other parameters of pulses supplied on the channel is preferably controlled taking into account the pulsed power supplied on the other channels e.g. the rate and/or other parameters of pulses supplied thereon. The channels may be wired or wireless channels, or a combination thereof. Preferably the channels are wired channels.

The external apparatus may have any desired number of transmitter coils. This will depend upon the number of receiver coils present in an implantable apparatus to which the external apparatus is to deliver power. One receiver coil is provided in respect of each transmitter coil. Thus, each transmitter coil is arranged to define a transmitter-receiver coil pair with a single one of receiver coils in use. However, it has been found that from 2 to 4 transmitter coils may be particularly suitable. There will therefore be from 2 to 4 power supply channels provided, one channel being provided in respect of each transmitter coil. In some preferred embodiments a single pair of transmitter coils is provided. For example, in some exemplary arrangements, a pair of transmitter coils may be provided to be mounted to the body of a user at different locations on the chest wall. A further pair of transmitter coils may additionally be provided for mounting to the body of the user at different locations on the abdomen.

The external apparatus of the invention in any of its aspects or embodiments includes dedicated power supply channels associated with each of the respective transmitter coils. The provision of multiple power supply channels enables pulses to be supplied to different ones of the transmitter coils over the respective power supply channels at different times. Power may be supplied over a selected one or ones of the power supply channels defining a subset of the plurality of channels.

Preferably the power supply means of the external transmitter apparatus comprises control means for controlling the supply of power over the different channels (i.e. to the transmitter coils) of the transmitter apparatus. The control means may be arranged to distribute the supply of power to the transmitter coils over the plurality of channels and/or to control the timing of pulses in the pulsed power supply delivered to the transmitter coil on each given channel. The method of the invention in its various aspects may extend to distributing the supply of power to the coils and/or controlling the timing of pulses provided on each given channel to the transmitter coil associated therewith using the control means. The control means may be arranged to control the parameters of the pulsed power supply on each channel e.g. the parameters relating to the pulses, such as duration, interval between pulses etc. The control means may be arranged to control the power supply on each channel in any suitable manner. In embodiments the control means may be arranged to control the operation of the switching means associated with a channel where such switching means is provided.

In preferred embodiments the control means is arranged to control a timing of the pulses of the pulsed power supply provided on different ones of the plurality of channels. The control means is able to control the timing of the pulses provided on each of the different channels, although in use, a pulsed power supply may not always be delivered over all of the channels. Thus, the control means will, in use, control the timing of the pulses on each active channel. The control means may comprise a set of one or more processors.

The control means is preferably arranged to control the timing of the pulses of the pulsed power supply over each of the different channels such that pulses are provided on different ones of the channels at different times. The pulses may be provided on the channels one at a time. The order of the channels over which the pulses are provided may or may not then be fixed. The control means may thus be arranged to control the timing of the pulses of the pulsed power supply provided over the plurality of channels such that pulses are provided on less than all of the channels at a given time, and preferably on only a single channel at a given time.

The control means is preferably arranged to control the timing of the delivery of the pulses of the pulsed power supply provided on each of the different channels such that there is no overlap in time between pulses provided on any ones of the different channels. An overlap in time between pulses refers to any overlap in the duration of pulses i.e. between the start and the end of the pulse. The control means ensures that there is never any overlap in time between pulses delivered on any of the different channels. In this way, it may be ensured that no two or more channels are transmitting pulses i.e. power at the same time. In particularly preferred embodiments the control means is arranged to control a timing of the pulses of the pulsed power supply over different ones of the plurality of channels such that each channel has a different respective timeslot in which pulses are provided over the channel. In other words, pulses are delivered to the transmitter coils over each one of the channels in a different respective timeslot associated with that channel. The timeslots are selected such that there is no overlap in time between pulses provided on different channels. A pulse may be provided over a channel for a duration less than the duration of that channel's timeslot. In this case, there may be no overlap in time between timeslots associated with different channels. Pulses may be delivered on the different channels sequentially (though not necessarily in any fixed order). The timeslots may be chosen such that the frequency of delivery of pulses on one channel is different to that on another channel. For example, one channel may have a timeslot that is an integer multiple of a timeslot on another channel.

References to a pulsed power supply or a pulse being provided on or over a channel are interchangeable.

The method of the invention in any of its aspects or embodiments may comprise controlling the timing of the delivery of the pulsed power supply (e.g. using a control means) such that pulsed power is delivered in any of the above manners. The result is that pulses are preferably not supplied on more than one channel at the same time, or so as to overlap in time.

The above steps refer to the timing of the delivery of pulses to the transmitter coils over all of those different channels which are active i.e. over which a pulsed power supply is supplied at any given time. As discussed below, power supply on one or more of the channels may be temporarily disabled in certain circumstances. In normal operation only a subset of power supply channels may be temporarily disabled at any given time, to ensure that power may still be delivered over at least one, and preferably multiple channels.

The invention may extend to an implantable receiver apparatus for the TET system receiving pulses through one or more of the receiver coils thereof in accordance with any of the above methods e.g. such that a pulse is received on only one channel at a time.

Alternatively or preferably additionally, in preferred embodiments the control means is arranged to be able to temporarily disable the delivery of a pulsed power supply on one or more of the channels. The control system may be arranged to be able to temporarily disable any one or more of the channels at any given time. Thus, a subset of the channels may be active at a given time. The method may comprise temporarily disabling delivery of a pulsed power supply on one or more of the channels (e.g. using a control means). This refers to the provision of a power supply comprising a series of pulses, rather than the timing of individual pulses. A channel is active when a pulsed power supply is delivered thereto, even though there will then be gaps between the pulses. Disabling a channel does not merely refer to the gap between pulses.

The method of operating the implantable receiver apparatus extends to the receiver coils of the apparatus receiving pulses in any of the above manners, i.e. such that pulses received by the coils do not overlap etc. Each receiver coil receives power over a given channel, and the pulses will therefore have the timing and other properties with which they were provided to the power supply channel associated with the transmitter coil.

In preferred embodiments power supplied to the transmitter coils over the channels is controlled at least in part using data obtained from a feedback arrangement. The timing of the pulses provided over the channels and/or the distribution of the supply of power over the channels may be controlled at least in part using the data obtained from the feedback arrangement. In some preferred embodiments a determination to temporarily disable the power supply over a given channel or channels may be based on the feedback data.

The supply of power to the transmitter coils over the plurality of channels may be controlled e.g. by the control means based at least in part upon received data relating to one or more of; the operation of the implantable receiver apparatus of the TET system, the operation of the implantable medical device, the operation of an implantable rechargeable backup battery associated with the implantable medical device (where provided), an alignment between the transmitter coils of the external transmitter apparatus and the receiver coils of the implantable apparatus, and the temperature of the skin of the user. Data relating to the operation of the implantable rechargeable backup battery may relate to the battery charge level, whether the battery is undergoing charging etc. Data relating to the operation of the implantable medical device may be indicative of any failure of the device, or, by way of example, for an LVAD type device, a blood pumping volume etc. Preferably the supply of power is controlled based at least on the temperature of the skin of the user. The method may extend to controlling the supply of power to the transmitter coils based upon any such received data. A control means of the power supply means for controlling the supply of power to the transmitter coils over the plurality of channels may be capable of controlling the supply of power over the channels based upon received data relating to any of these factors. The data may be received from a power management system of the implantable receiver apparatus of the TET system as described below.

Preferably a power management system of the implantable receiver apparatus of the TET system is arranged to transmit data to the external apparatus of the TET system relating to one or more of; the operation of the implantable receiver apparatus of the TET system, the operation of the implantable device, the operation of an implantable rechargeable backup battery associated with the implantable medical device, an alignment between the transmitter coils of the external transmitter apparatus and the receiver coils of the implantable apparatus, and the temperature of the skin of the user, for use by the external transmitter apparatus e.g. by a control means of the power supply means in controlling the supply of power to the transmitter coils over the plurality of channels. In preferred embodiments the data is transmitted over a dedicated wireless feedback channel.

The temperature of the skin of the user may be indicative of an external, or more preferably an internal skin temperature of the user. The data indicative of the temperature of the skin of the user is preferably indicative of the temperature of the skin of the user i.e. in the vicinity of each transmitter-receiver coil pair. It will be appreciated that each transmitter coil of the external transmitter apparatus forms part of a transmitter-coil pair in use. The temperature of the skin in the vicinity of a transmitter-receiver coil pair corresponds to the temperature in the vicinity of a transmitter coil of the external transmitter apparatus or in the vicinity of a receiver coil of the implantable receiver apparatus, and references to the temperature in the vicinity of a transmitter-receiver coil pair may be replaced by a reference to a temperature in the vicinity of the transmitter or the receiver coil as appropriate. The temperature will be indicative of the temperature of the skin in the vicinity of a particular power supply channel.

In some embodiments the implantable receiver apparatus of the TET system comprises means for measuring the internal temperature of the skin of the user in the vicinity of each transmitter-receiver coil pair. A temperature sensor is preferably provided in respect of each receiver coil. Of course, in other embodiments, means may alternatively or additionally be provided for measuring the temperature of the skin in the vicinity of each transmitter-receiver coil pair e.g. a temperature sensor may be associated with each transmitter coil. Such sensors would then be associated with the external apparatus.

In preferred embodiments the control means of the external transmitter apparatus is arranged to control the supply of power over a channel based upon data indicative of a temperature of the skin of a user i.e. in the region of the transmitter-receiver coil pair associated with the channel. As mentioned above, the temperature data may relate to an internal or external temperature of the skin i.e. as sensed on the external transmitter or implantable receiver side, and most preferably on the implantable receiver side. The control means may be arranged to temporarily disable power supply over a power supply channel associated with a transmitter coil, where the temperature of the skin in the region the transmitter-receiver coil pair of which it forms part exceeds a threshold temperature. The power supply over the channel may be ceased until the temperature of the skin is found to have decreased by a given amount, e.g. to or below the threshold temperature. Alternatively or additionally the control means of the external apparatus may be arranged to vary a rate of the energy pulses delivered over a power supply channel to the respective transmitter coil associated therewith based on received data indicative of a temperature of the skin in the region of the transmitter-receiver coil pair including the transmitter coil. Where the temperature of the skin in the region of a transmitter-receiver coil pair exceeds a threshold temperature, the control means may be arranged to decrease a rate of the energy pulses delivered over the channel associated with the transmitter coil forming part of the transmitter-receiver coil pair. The control means may additionally increase a rate of the energy pulses delivered over one or more of the channels, or each channel, associated with another transmitter coil of the apparatus i.e. to compensate for the reduced power that will be received over the affected channel.

Other data transmitted for use in controlling the power supply over the channels or otherwise may be indicative of the power received by a receiver coil, the alignment of a transmitter coil with a receiver coil (which may be sensed from the implanted side by reference to the received power) the detection of an emergency situation, the detection of a fault, the charge level of a rechargeable backup battery associated with the implantable device, the power demands of the implantable device etc. Data may be obtained by one or more sensors and/or monitoring circuitry of the implantable receiver apparatus of the TET system. For example, where coupling between a transmitter-receiver coil pair is interrupted, or decreases, e.g. due to increased spacing between the coils, or a coil becoming disconnected from the body, or a misalignment between the transmitter and receiver coils, data indicative of this may be transmitted to the external apparatus to enable power supplied on that, or other channels to be increased as appropriate to try to continue to meet the demands of the implantable device. If a fault or emergency condition is detected, e.g. if the device is found to be operating outside of a safe operating range, the control means may at least temporarily cease delivery of power to the implantable device over any of the channels.

The power supplied over each one of the channels by the power supply means to the transmitter coils of the external apparatus is a pulsed power supply. The pulses on each given channel have a given duration and are separated by intervals in which no power is supplied on the channel. The pulses are preferably RF pulses. The frequency of the RF within each pulse is preferably at least 100 kHz, or at least 150 kHz. The frequency of the RF within each pulse is preferably less than 300 kHz. The frequency of the RF within each pulse is preferably in the range of from 100-300 kHz, such as at 200 kHz. Preferably each of the channels operates at the same frequency. The frequency of the RF pulses on a given channel may be defined by appropriately tuning the transmitter coil associated therewith. The above ranges are merely exemplary of some preferred ranges of operation, and it will be appreciated that it not essential that operation is within these ranges. The skilled person will readily be able to determine suitable operating parameters for a particular arrangement.

The following parameters may be applied to the pulses applied on any one or one of the channels, and preferably to the pulses applied on each channel over which a pulsed power supply is delivered. The power supply means of the external transmitter apparatus is operable to supply pulses on the channel or channels within any of the following ranges, and the method may comprise supplying pulses on any of the channels within any one or ones of the following ranges to the extent that they are not mutually exclusive. The method will involve supplying pulses on ones of the at least some of channels i.e. the active channel(s) in this manner. A control means of the power supply means may be used to set the parameters of operation on each channel. The following ranges are merely exemplary of some preferred ranges of operation, and it will be appreciated that it not essential that operation is within these ranges. The skilled person will readily be able to determine suitable operating parameters for a particular arrangement. It will be appreciated that the parameters relating to the pulses on different channels may be set the same for each channel, or may vary between channels. Furthermore, parameters in relation to a particular channel may be varied during operation e.g. in response to feedback.

The duration of each pulse is preferably at least 10 ms. The duration of each pulse is preferably less than 100 ms, and more preferably less than 50 ms. In some embodiments the duration of each pulse is in the range of from 10 ms to 100 ms, and most preferably from 15 ms to 30 ms.

The rate at which pulses are provided on a channel is preferably within the range of from 0.03 Hz to 10 Hz. In other words, the frequency that the pulses are provided on the channel may be in this range. The rate of the pulses provided on a given channel may be a variable rate in this range.

The energy supplied per pulse may be in the range of from 0.3 J to 30 J, such as 18 J.

The rate of delivery of the pulses, and the duration of the pulses, may be selected appropriately to provide a suitable time interval in which power is not supplied over the channel to enable the skin in the region of the transmitter coil to cool. This may help prevent overheating of the skin.

The time interval between consecutive pulses on a channel may be in the range of from 100 ms to 30 s. This time interval provides a skin cooling time for the skin temperature to decrease between applied pulses. The interval between pulses on a given channel to provide a desired amount of skin cooling may be determined by reference to a number of heart beats, since blood circulation provides a coolant effect. For example, to allow for the cooling which may be provided by about 9 heartbeats would require an interval of around 8 seconds. It will be appreciated that the time interval between pulses on different channels may, and in some embodiments is, set differently, preferably within the above range. The interval between pulses on a channel may be a variable interval in the above range.

While the duration of pulses on a given channel may be varied to control the energy delivered on the channel, preferably the duration of the pulses on each channel is fixed, and the energy delivered on a channel is controlled by varying the interval between pulses delivered on the channel. The interval between pulses in different channels may be set differently. For example, the interval between pulses on one channel may be an integer multiple of the interval between pulses on another channel.

The pulsed power supply provided on the or each channel may be controlled e.g. the parameters thereof are set, so as to maintain a power input to the implantable medical device above a pre-determined threshold (e.g. the power rating of the implantable medical device). Maintaining a power input above a pre-determined threshold may comprise maintaining a voltage input provided to the implantable device above the voltage required by the implantable medical device.

In particularly preferred embodiments, where power is supplied over multiple channels, the timing of the pulses on each channel over which power is supplied is related to the timing of the pulses on each other channel over which power is supplied. Preferably, where power is supplied over multiple channels, the timing of the pulses on each channel is set so as to maximise the time interval between the end of a pulse provided on one channel and the start of the next pulse delivered on any one of the channels e.g. whilst maintaining a continuous supply of power to the implantable medical device. Maintaining a continuous supply of power to the implantable medical device may comprise maintaining a power input to the implantable medical device above a pre-determined threshold (i.e. the power rating of the implantable medical device). Maintaining a power input above a pre-determined threshold may comprise maintaining a voltage input provided to the implantable device above the voltage required by the implantable medical device. The method may comprise controlling the timing of the pulses provided on the channels in this manner. The parameters relating to the pulses on any one of the channels will still preferably be within the above described ranges.

In accordance with the invention in any of its aspects or embodiments the transmitter coils may be of any conventional type. For example, a spiral copper coil may be used. However, it is envisaged that the transmitter coils could also be of the new construction described below, including at least one flexible coil layer. Each transmitter coil may be provided with means for securing the transmitter coil to the skin of a user or to a wearable garment for locating the coil in proximity to a receiver coil of an implantable apparatus of the TET system as described above.

Preferably each transmitter coil is arranged to provide a resonant coupling to the receiver coil associated therewith at the frequency of RF pulses of the pulsed power supply supplied to the transmitter coil over the power supply channel associated therewith by the power supply means. This frequency may be considered as the operating frequency of the system. These tuned arrangements may increase efficiency of energy transfer to the receiver apparatus.

Each transmitter coil may form part of a tuned circuit to enable it to provide a pulsed power supply comprising RF pulses of a given RF frequency. The tuned circuit associated with a transmitter coil may be set to have a resonant frequency matching a resonant frequency of a tuned circuit associated with the receiver coil that receives power from the transmitter coil. In preferred embodiments the or each tuned circuit of the transmitter apparatus is a parallel tuned circuit. The or each tuned circuit is preferably an LC tuned circuit. Each transmitter coil is preferably tuned to the same RF frequency.

Each transmitter coil is arranged to transmit power to a given one of a plurality of receiver coils of the implantable receiver apparatus of the TET system with which it is in proximity in use. The transmitter and receiver coils are inductively coupled to one another through the skin of the user in use. The coupling is at least through the skin of the user, and may be through any additional layers which are present between the transmitter and receiver coils e.g. a layer of a wearable garment in embodiments where the transmitter coil is mounted to a wearable garment. The coils of the external apparatus and the implantable device thus define a plurality of transmitter-receiver coil pairs. When the external apparatus is positioned with respect to the body of a user, each transmitter coil is arranged to transmit power only to a single given receiver coil of the implantable receiver apparatus with which it is in proximity. Each one of the power supply channels of the external apparatus is therefore associated with the delivery of power to a particular one of the receiver coils of the implantable device. In general, a transmitter coil is able to transmit power to a receiver coil of the implantable receiver apparatus when it is aligned therewith i.e. axially aligned. The coils should also be located appropriately with respect to the skin interface on either side thereof to be within a range that permits coupling between the coils. The transmitter and receiver coils of a transmitter-receiver coil pair will face one another on opposite sides of the skin of the user.

A corresponding number of transmitter and receiver coils will be present in the external transmitter apparatus and the implantable receiver apparatus of the TET system to enable one to one coupling between transmitter and receiver coils. Thus there may be from two to four receiver coils, or, in some embodiments, a single pair of receiver coils.

Turning to the implantable receiver apparatus, in those aspects or embodiments of the invention relating thereto, each receiver coil preferably forms part of a tuned circuit of the receiver circuitry. The tuned circuit may be tuned to the RF frequency of RF energy pulses of the power supply delivered to the coil by the transmitter coil associated therewith. The RF frequency of a pulse refers to the frequency within each pulse, rather than the frequency at which pulses are delivered on a channel. The implantable receiver apparatus may be arranged such that each receiver coil may be independently tuned to an RF frequency of RF energy pulses of the power supply delivered thereto. This will enable RF energy pulses of different frequencies to be applied to different receiver coils, e.g. with each transmitter coil providing RF energy pulses of different frequencies. Independently tunable circuits associated with the receiver coils may also allow tuning of the individual receiver coils to be modified based upon the operation of the individual respective coils. However, for ease of operation, each transmitter coil may be arranged to provide RF energy pulses of the same frequency, and each receiver coil tuned to the same RF frequency. In preferred embodiments the or each tuned circuit of the receiver apparatus is a parallel tuned circuit. The or each tuned circuit is preferably an LC tuned circuit.

In embodiments the implantable receiver apparatus of the TET system comprises means for rectifying the pulsed power supply received by each receiver coil from a transmitter coil of the external apparatus. The rectifying means may be any suitable circuitry e.g. comprising a set of one or more diodes. Rectifying means is preferably provided in respect of each receiver coil. The rectifying means converts received AC pulses of the power supply into DC pulses. The receiver apparatus may further comprise means for filtering e.g. smoothing an output of the rectifying means. The filtering means is preferably passive filtering means i.e. that does not include any active components. Filtering circuitry may be provided in respect of the rectifying means for each coil.

In preferred embodiments each receiver coil of the receiver apparatus forms part of a respective power receiving channel of the receiver apparatus i.e. dedicated to that receiver coil. One such power receiving channel is associated with each receiver coil. In the preferred embodiments in which rectifying means, and, where provided, filtering means, is provided in respect of each coil, rectifying means and filtering means is thus associated with each channel. The power received over a given channel may then be processed independently of power received over the other channels. In use each power receiving channel is associated with i.e. forms a continuation of, a given one of the power supply channels associated with the transmitter coil that defines a transmitter-receiver coil pair with the receiver coil.

In preferred embodiments each receiver coil of the implantable receiver apparatus is connected to a respective flexible power delivery lead of the implantable receiver apparatus for transporting power away from the coil. The power delivery lead may be of any suitable length, depending upon the size of the user it is intended for. In some embodiments rectifying and/or filtering means for the coil, and preferably both rectifying and filtering means, is associated with each flexible power delivery lead. The components of the rectifying and/or filtering means, and preferably of both the rectifying and filtering means, are preferably distributed along the length of the lead. The rectifying and filtering means may be distributed along respective portions of the length of the lead. The components should be provided in such a manner that maintains a flexibility of the lead. The flexible power delivery lead may have a proximal end and a distal end, the proximal end being connected to the receiver coil, wherein the rectifying means is preferably provided by a set of diodes distributed along a proximal portion of the lead. The filtering means, where present, is provided distal to the rectifying means. The rectifying means may be associated with a first proximal portion of the length of the lead, and the filtering means with a second portion of the length of the lead distal thereto. The first portion may be of greater diameter than the second portion. The rectifying means may be distributed along the length of the first portion, and the filtering means along the length of the second portion. The second portion may not extend to the distal end of the lead. The filtering means may be provided by a set of parallel capacitors, such as a flexible strip of capacitors attached to the lead, or may be integral with the lead. For example, the filtering means may be provided by a length of coaxial cable forming part of the lead e.g. defining a second portion thereof.

In other embodiments however, the rectifying and/or filtering means may be provided separately to the lead. In this way, a relatively simple lead may be provided. It has been found that in some contexts at least this may be more economical and/or reliable, i.e. less prone to failure, than a lead with distributed rectifying and filtering means, which may be advantageous in certain applications. In some embodiments rectifying and/or filtering means may thus be provided downstream of the lead.

The flexible lead may, for example, have a length in the region of from 15 cm to 80 cm. The most appropriate length will depend upon the application and the size of the user, and the intended position of the receiver coil when implanted.

The lead may comprise a flexible outer sheath, such as a polyurethane sheath.

A distal end of the lead may comprise one or more output terminals e.g. wires. Preferably each receiver coil is connected to a tuning capacitor arrangement for tuning the resonant frequency of the receiver coil circuit. The resonant frequency of the receiver coil circuit is preferably selected based on the operating frequency of a transmitter coil circuit with which the receiver coil communicates. The resonant frequency of the receiver coil circuit may also depend upon the number of turns of the coil. Preferably the tuning capacitor arrangement forms part of the flexible lead. The tuning capacitor arrangement is preferably provided as a flexible strip which is integrated into the lead e.g. at a proximal end of the lead.

Of course, other circuitry may be provided for processing the power supply received by each receiver coil. Means may be provided for protecting the implantable device from an overvoltage e.g. in the event of an open circuit operation of the system. In some embodiments voltage limiting means is provided in respect of each receiver coil. The voltage limiting means may comprise a set of capacitors. The set of capacitors may be arranged in parallel with a set of capacitors providing filtering of the power supply received by the receiver coil. In preferred embodiments in which the receiver coil is connected to a flexible power delivery lead, the voltage limiting means is associated with the power delivery lead.

Preferably the implantable receiver apparatus comprises a power management system, and is arranged such that each receiver coil delivers power received from a transmitter coil of the external transmitter apparatus to the power management system. The power management system may be a power management unit. For example, a distal end of a power delivery lead associated with each receiver coil may be connected to the power management system. The power management system is preferably arranged to receive power from each of the receiver coils. The power is received by the power management system after any rectification and filtering has been carried out.

The power management system may be arranged to combine power supplies received from the plurality of receiver coils of the implantable receiver apparatus, and distribute power as required to an implantable medical device when connected to the implantable receiver apparatus of the TET system. The power management system may be arranged to control a voltage of power supplied to the implantable medical device. In some embodiments the implantable receiver apparatus of the TET system is connected to a rechargeable backup battery for the implantable medical device, such as a lithium ion battery, and the power management system is arranged to selectively provide received power to the implantable medical device and/or to the rechargeable backup battery. It will be appreciated that the power management system may provide power to both the rechargeable backup battery and the implantable medical device simultaneously. In this case, generally, the power supply to the implantable medical device will have priority.

The power management system may also be arranged to selectively provide power from the rechargeable backup battery to the implantable medical device. The power management system may comprise a housing. The housing may house circuitry for performing the functions of the power management system.

In accordance with the invention in any of its aspects or embodiments, the implantable receiver apparatus may form part of an implanted system comprising the implantable receiver apparatus and an implantable medical device, and optionally a rechargeable backup battery for the implantable medical device. It will be appreciated that both the implantable medical device, and a rechargeable backup battery, where provided, are preferably connected or connectable to the implantable receiver apparatus of the TET system via a power management system thereof.

The implantable receiver apparatus preferably comprises means for converting the or each pulsed energy supply received from the receiver coils to a continuous power supply for use in powering the implantable medical device. The power management system may be arranged to perform such a function, and to otherwise process the received transmissions e.g. signals to provide a suitable power supply for the implantable device, and/or a rechargeable backup battery where provided.

In preferred embodiments, whether or not a rechargeable backup battery is provided, the implantable receiver apparatus is arranged such that power received by each receiver coil is delivered to energy storage means for temporary storage prior to use in energising an implantable medical device and/or rechargeable backup battery. Thus energy may be stored prior to the power being supplied to the implantable medical device and/or to a rechargeable backup energy storage device, where provided. Preferably the power is stored by the energy storage means prior to being supplied by the power management system to the implantable medical device and/or an implantable rechargeable backup battery for the device. The power is preferably stored after any rectification and/or filtering.

An energy storage means may be provided common to all of the receiver coils. Thus, a single energy storage means may be provided for each of the power receiving channels. Providing a common energy storage means for each of the channels may be more efficient in some contexts at least than providing a plurality of individual energy storage means associated with respective receiver coils, and may also be more practical for an implantable system as it may be less bulky and simpler for the power management system to handle. Nonetheless, in other embodiments, multiple energy storage means may be provided e.g. with an energy storage means in respect of each receiver coil, or with multiple energy storage means in respect of respective ones of a plurality of different subsets of the plurality of receiver coils. Each subset may include one or a plurality of the receiver coils.

In these embodiments, each power receiving channel, or each subset of power receiver channels, of the implantable apparatus may thus be associated with an individual respective energy storage means. In this case the power management system may merge the outputs from each of the energy storage means before providing the supply of power to the implantable device and/or backup battery.

In embodiments in which a rechargeable backup battery is provided, the storage device is used to power the implantable device when power received from the external transmitter apparatus does not meet the requirements of the device. This may occur when the external transmitter apparatus has been temporarily disconnected from the body of a user, e.g. while the user washes, or where coupling between transmitter and receiver coils is interrupted or reduced for any reason. Of course, it is not necessary that such a rechargeable backup battery is necessarily provided, and it is not an essential feature that the implantable receiver apparatus of the TET system is connected or connectable to such a device.

The applicant has realised that rechargeable backup batteries have some drawbacks. Batteries typically have a limited lifetime i.e. number of recharge cycles, and are only capable of continuously driving a higher power rated implantable device for a limited period. This is due to the relatively low power density associated with conventional batteries. For example, lithium ion batteries can typically only power an 8 W LVAD (left ventricular assist device) type device for around 20 minutes. A battery may have a cycle lifetime of only around 400 cycles. Batteries also tend to be relatively heavy and bulky, which is disadvantageous in the context of an implanted device.

The Applicant has found that capacitor arrangements may be used to store energy, and may overcome some of these problems. A suitable capacitor arrangement will have a relatively higher power density than a conventional backup battery, and will be relatively less bulky. Capacitors may be charged virtually instantly, and have a substantially unlimited cycle lifetime. Nonetheless, the energy capacity of a capacitor arrangement will be relatively smaller than that of a typical backup battery. The Applicant has realised that by incorporating a suitable capacitor arrangement in the implantable apparatus for temporarily storing energy received from a coil, instead of, or in addition to a backup battery, operation of the TET system may be significantly improved.

The features described below in relation to the energy storage means are applicable to each energy storage means, whether a single, or multiple such energy storage means are provided. The or each energy storage means may be of the construction described. Whether or not a rechargeable backup battery is provided, preferably the or each energy storage means for temporarily storing power received by a receiver coil or coils associated with the energy storage means comprises a capacitor arrangement. Preferably therefore, the implantable receiver apparatus is arranged such that power received by each receiver coil is delivered to a capacitor arrangement for temporary storage prior to use in supplying power to an implantable medical device. This may be prior to the power being supplied to the implantable medical device and/or to a rechargeable backup battery, where provided. Preferably the power is stored by the or each capacitor arrangement prior to being supplied by the power management system to the implantable medical device and/or an implantable rechargeable backup battery for the device. Preferably the capacitor arrangement is a supercapacitor arrangement. In embodiments, the supercapacitor arrangement comprises an arrangement of solid state or electrochemical double layer capacitors. In some embodiments, as described above, one capacitor arrangement e.g. supercapacitor arrangement is provided common to all receiver coils. Thus, each of the power receiving channels may share a single capacitor arrangement. In other embodiments however, multiple capacitor arrangements may be provided. One capacitor arrangement e.g. supercapacitor arrangement may be provided in respect of each receiver coil or in respect of a subset of the plurality of receiver coils. Thus each power receiving channel, or each subset of power receiver channels, of the implantable apparatus may comprise a respective own capacitor arrangement.

A capacitor arrangement may be arranged to receive power from a receiver coil or coils after it has been subjected to any rectification and/or filtering. In preferred embodiments the capacitor arrangement is arranged to temporarily store power prior to the power being provided by a power management system of the implantable receiver apparatus to the implantable medical device and/or an implantable rechargeable backup battery for the device. The capacitor arrangement may be disposed between the receiver coil and the power management system of the implantable receiver apparatus. The arrangement may then store power (e.g. after the rectifying and filtering means of the or each coil with which it is associated, where such means are provided) prior to it being provided to the power management system. The capacitor arrangement may be connected to a distal end of a flexible power delivery lead associated with the receiver coil in preferred embodiments in which the receiver coil is connected to such a lead. In other embodiments in which a power management system is provided, the or each capacitor arrangement may be provided within a housing of the system e.g. at an input thereof. The arrangement may then store power prior to it being used by the power management system.

In contrast to a conventional backup battery, a capacitor arrangement may need to be more frequently recharged due to its relatively small energy capacity. However, this may easily be achieved using the pulsed power supply of the present invention. Such a power supply may be readily used to deliver relatively large energy pulses with at a rate required to recharge the capacitor arrangement. The power supply arrangement of the external transmitter apparatus of the present invention, i.e. a multi-channel pulsed power supply is therefore particularly effective when used with an implantable receiver apparatus that includes such a capacitor arrangement, and allows the implantable receiver apparatus to exploit such a capacitor arrangement, with the benefits this may provide. The rate of the pulses delivered to a receiver coil, and hence to the capacitor arrangement associated therewith for recharging the capacitor arrangement, may be controlled to allow the capacitor arrangement to deliver a desired amount of power. The rate may also be controlled to enable the capacitor arrangement to deliver a continuous power supply for use by the implantable medical device i.e. by ensuring a continuous discharge of the capacitor arrangement. It will be appreciated that as the energy pulses required to meet the overall power requirements of the implantable device are provided over multiple channels in accordance with the invention, it is possible to increase the amount of energy transferred per pulse, while still avoiding skin overheating problems, as the amount of time over which energy need be supplied on one particular channel is reduced i.e. there are intervals between pulses in which skin may cool.

The or each capacitor arrangement (which is preferably a supercapacitor arrangement) may include one or more capacitors. Where multiple capacitor arrangements are present e.g. in respect of each receiver coil, each may be in accordance with any of the embodiments discussed below. The arrangement may consist of a single capacitor, or a bank of two or more capacitors. The bank may comprise capacitors arranged in series and/or parallel. A given capacitor arrangement may include any number of capacitors connected in any manner to provide an appropriate overall capacitance and voltage. For example, a capacitor arrangement may include from 1-8 capacitors. The appropriate number of capacitors and the way in which they are connected i.e. in series and/or parallel, will depend upon the capacitance and voltage specifications of the capacitor used. The capacitor arrangement may be constructed to minimise volume. Reduced bulk is advantageous in the context of the implantable apparatus. In embodiments the capacitance of the capacitor arrangement is at least 10 mF. In embodiments the capacitance of the capacitor arrangement is less than 5 F. In preferred embodiments the capacitance of the capacitor arrangement is in the range of from 10 mF to 5 F. The capacitor arrangement may have a voltage rating in the range of from 3.5V to 24V. The capacitor arrangement should have a voltage rating selected as appropriate depending upon the voltage required by an implantable device that is used with the implantable receiver apparatus. The above ranges and configurations have been found to be applicable to any capacitor arrangement provided, whether it is associated with one or more receiver coils.

Of course, it will be appreciated that the use of a capacitor arrangement is not essential. However, the provision of a capacitor arrangement is advantageous as this allows power to be stored and then sustainably delivered to the implantable device, reducing the likelihood of needing to resort to a backup battery where provided. The capacitor arrangement may simultaneously perform the function of converting a pulsed energy supply to a continuous supply suitable for provision to the implantable medical device.

In some preferred embodiments in which each receiver coil is connected to a flexible power delivery lead, a proximal end of the power supply lead is preferably connected to the receiver coil and a distal end of the power supply lead is preferably connected to the power management system, or where provided, to a capacitor arrangement for temporarily storing power for use by the power management system.

In embodiments in which a rechargeable backup battery is connected to the implantable receiver apparatus, power received from one of the receiver coils may be dedicated to recharging the backup battery. For example, a power management system may direct power received from the receiver coil to the backup battery. The method may comprise using the power received from a receiver coil in this way. It will be appreciated that one of the channels associated with a transmitter coil of the external apparatus may therefore be dedicated to providing power for recharging a backup battery for the implantable medical device. The other channel(s) may be used to provide power for directly powering the implantable medical device.

The implantable medical device with which the TET system, implantable receiver apparatus or external transmitter apparatus for a TET system, of the present invention in its various aspects or embodiments, or with which the external apparatus may be used, or the implantable apparatus connected, may be of any suitable type. In some preferred embodiments the implantable medical device is a cardiac implantable device. The implantable device may be a cardioverter device, an artificial heart, an artificial heart pump such as a ventricular assist device (VAD), which may be a left, right or bi-ventricular assist device, although preferably is an left assist device i.e. LVAD, a cardiac defibrillator, an atrioverter defibrillator e.g. passive implantable atrioverter defibrillator (PIAD) device, or a pacemaker. However, the present invention is applicable more generally to other types of implantable medical device that requires a power supply, such as an artificial lung, artificial urinary bladder, an implanted permanent ventilator, an artificial kidney, or to an implantable drug delivery system. The invention in relation to the TET applications is particularly applicable to those implantable medical devices that require a sustained power supply at a higher level.

The implantable device is preferably a device having a power requirement of greater than 2 W.

Each receiver coil may be associated with means for mounting the coil to the body of a wearer i.e. in proximity to a respective transmitter coil of an external transmitter apparatus of the TET system in use. For example, each receiver coil may comprise means for adhesively mounting the coil to the body. Each receiver coil of the implantable apparatus is preferably locatable in a different position with respect to the body of the wearer, and is preferably independently locatable. Each receiver coil may be associated with a particular anatomical location in use. Each receiver coil may be locatable in a respective one of the following locations of the skin; the waist or abdominal area, the upper left chest wall, and the upper right chest wall. The different receiver coils may be locatable in two or more of these locations simultaneously. The locations of the receiver coils may correspond to any of the locations described in relation to the transmitter coils of the external transmitter apparatus and vice versa. The locations will correspond to the locations of the transmitter-receiver pairs of the overall TET system.

While the receiver coils of the implantable receiver apparatus may be of any conventional type, it is preferred that the receiver coils are of a particular construction that has been found to be particularly advantageous in the context of delivering power to an implantable medical device. In accordance with the invention in any of its aspects or embodiments relating to the implantable apparatus of the TET system, whether or not in combination with the external transmitter apparatus, each of the coils of the implantable apparatus of the TET system which receives power from the coils of the external transmitter apparatus is preferably a flexible coil which comprises at least one coil layer, comprising a coil portion printed on a flexible substrate.

This type of coil construction has been found to be advantageous in reducing bulk of the receiver coils. This is an important consideration for an implantable receiver coil, as space within the body is limited, e.g. within the chest cavity. As the coils are defined by one or more printed flexible substrate layers, rather than using a conventional mechanically wound coil, it is possible to increase the effective area of the coil available for coupling to an external transmitter coil without substantially increasing the bulk of the coil. This may enable improved coupling to be obtained, in the context of a coil which is also able to readily conform to the body e.g. to the interior of a chest wall. Better conformance to the applicable interface within the body further helps to enhance coupling with an external transmitter coil.

It is believed that an implantable receiver apparatus for a TET system having such receiver coils is advantageous in its own right.

From a further aspect of the invention there is provided an implantable receiver apparatus for a TET system, the implantable apparatus being connected to an implantable medical device and comprising one or more flexible receiver coil, each receiver coil being arranged to receive power from a coil of an external transmitter apparatus of the TET system when in proximity thereto in use for energising an implantable medical device when connected to the implantable apparatus, wherein each of the receiver coils of the implantable apparatus comprises at least one coil layer comprising a coil portion printed on a flexible substrate.

It will be appreciated that the present invention in accordance with the further aspect may include any or all of the features described in relation to any of the embodiments of the earlier aspects of the invention to the extent they are not mutually inconsistent therewith, and vice versa.

The present invention in this further aspect extends to a TET system comprising the implantable receiver apparatus and further comprising an external transmitter apparatus comprising one or more transmitter coils for transmitting power to the at least one receiver coil of the implantable apparatus. The transmission may be continuous or pulsed. A pulsed power transmission i.e. power supply includes a series of pulses as described in the earlier aspects.

In these aspects relating to a TET system, power is of course transmitted transcutaneously i.e. wirelessly between the transmitter and receiver coils.

It is believed that the use of receiver coils of this construction in the context of an implantable receiver apparatus of an implantable medical device is advantageous in other contexts where an implantable receiver coil is required for use with an implantable medical device, not just when the coils are used to receive power as part of a TET system. For example, these arrangements may be used to provide a receiver coil of a cardiac defibrillator or more generally, of a pulse delivery device e.g. electric shock therapy device. A receiver coil of the construction of the invention in these further aspects and embodiments may be used with any type of transmitter system, not only the transmitter system of the TET system of the invention in its first aspect, and may be used with a transmitter system that does not form part of a TET system. The receiver coil may be tuned to any type of transmitter circuit, and may be customised to the size of a particular user. The receiver coil construction is advantageous in that it may be lightweight, slim, soft and flexible, and may be made of relatively small size e.g. of from 40-50 mm diameter. Receiver coils of this construction have been found to be less likely to decouple from the associated transmitter coils, as a result of their lightweight construction, and ability to conform to the body of the wearer. There is less likelihood of movement of the coil as a result of activities of the user, which may help to ensure greater transmission efficiency, and more efficient power control in embodiments relating to a TET system. In these further aspects, the transmission between the transmitter and receiver coils is again transcutaneous i.e. wireless.

From a further aspect of the invention there is provided an implantable receiver apparatus connected to an implantable medical device, the implantable receiver apparatus comprising one or more flexible receiver coil, each flexible receiver coil being arranged to receive a transmission from a coil of an external transmitter apparatus when in proximity thereto in use, wherein each of the flexible receiver coils of the implantable apparatus comprises at least one coil layer comprising a coil portion printed on a flexible substrate.

It will be appreciated that the present invention in accordance with the further aspect may include any or all of the features described in relation to any of the embodiments of the earlier aspects of the invention to the extent they are not mutually inconsistent therewith, and vice versa.

The present invention extends to the use of the implantable receiver apparatus of the invention in these further aspects or embodiments, and to such an implantable apparatus implanted into the body. The method may comprise the or each flexible receiver coil of the apparatus receiving a transmission from a coil of an external transmitter apparatus.

It will be appreciated that the present invention in accordance with the further aspect may include any or all of the features described in relation to any of the embodiments of the earlier aspects of the invention to the extent they are not mutually inconsistent therewith, and vice versa.

The invention may extend to a system comprising the implantable receiver apparatus and an external transmitter apparatus comprising one or more transmitter coil for providing a transmission to at least some of the one or more receiver coils of the implantable receiver apparatus. The method may comprise operating the external transmitter apparatus to provide a transmission that is received by a receiver coil of the apparatus.

The transmission in these further aspects or embodiments of the invention preferably comprises an RF pulse. In accordance with any of the aspects of the invention relating to a transmission by a transmitter coil, or the receiving thereof, a transmission, whether of an RF pulse or a power supply or otherwise, may be a signal.

References to the implantable apparatus being connected to an implantable medical device encompass the apparatus being attached to a separate medical device e.g. where it is an implantable apparatus of a TET system, or forming part of a medical device e.g. a defibrillator.

In some embodiments the implantable apparatus is an implantable receiver apparatus of a TET system, and each receiver coil is arranged to receive power from a coil of an external transmitter apparatus of the TET system when in proximity thereto in use for use in supplying power to an implantable medical device connected to the implantable receiver apparatus. In preferred embodiments the apparatus then comprises a plurality of the flexible receiver coils. Each receiver coil may be arranged to receive power from a given one of a plurality of transmitter coils of the external transmitter apparatus. The present invention in this further aspect extends to a TET system comprising the implantable receiver apparatus and further comprising an external transmitter apparatus comprising one or more transmitter coils, each being arranged to transmit power to a respective receiver coil of the implantable apparatus. The power transmission may be continuous or pulsed i.e. to provide a continuous or pulsed power supply.

It will be appreciated that the present invention in accordance with the further aspect may include any or all of the features described in relation to any of the embodiments of the earlier aspects of the invention to the extent they are not mutually inconsistent therewith, and vice versa.

In other embodiments the implantable receiver apparatus is an implantable receiver apparatus connected to a pulse delivery apparatus, wherein the implantable receiver apparatus is arranged to receive a RF pulse transmitted transcutaneously by an external transmitter apparatus of the pulse delivery apparatus in use and to use the received RF pulse in applying a pulse to implantable electrodes connected to the implantable receiver apparatus to enable a pulse to be delivered to the body when the electrodes are implanted in a part of the body in use. In this context a single receiver coil may be provided, or multiple receiver coils may be present. Preferably, in these embodiments, the implantable apparatus includes only passive components. In preferred embodiments the pulse delivery apparatus is a cardiac defibrillator apparatus, and the implantable receiver apparatus is arranged to use the received RF pulse in applying a defibrillator pulse to implantable electrodes connected to the implantable receiver apparatus to enable a pulse to be delivered to the heart when the electrodes are implanted in the heart in use. The cardiac defibrillator may be a passive implantable atrioverter defibrillator (PIAD). However, the pulse delivery apparatus may be an apparatus used in delivery a pulse to other parts of the body, such as the brain.

The present invention extends to a pulse delivery apparatus e.g. a cardiac defibrillator apparatus comprising the implantable receiver apparatus having one or more flexible receiver coils of these further aspects of the invention and an external transmitter apparatus, the external transmitter apparatus comprising a transmitter coil for transmitting an RF pulse to the receiver coil of the implantable receiver apparatus when in proximity thereto in use.

It will be appreciated that the present invention in accordance with the further aspect may include any or all of the features described in relation to any of the embodiments of the earlier aspects of the invention to the extent they are not mutually inconsistent therewith, and vice versa.

The present invention extends to a method of manufacturing the implantable receiver apparatus of any of the aspects or embodiments of the invention having one or more flexible receiver coils comprising at least one coil layer having a coil portion printed on a substrate, the method comprising the step of printing the or each coil portion on a respective flexible substrate.

It will be appreciated that the present invention in accordance with the further aspect may include any or all of the features described in relation to any of the embodiments of the earlier aspects of the invention to the extent they are not mutually inconsistent therewith, and vice versa.

It is expected that the particular flexible coil construction described above in relation to implantable receiver coils is also useful in the context of the transmitter coils of an external transmitter apparatus that is used with an implantable receiver apparatus connected to a medical device. Such a coil construction reduces the bulk of the transmitter coils, and may improve conformance to the body of the wearer, and hence coupling to a receiver coil of an implanted apparatus, in the same way described in relation to those aspects of the invention relating to the use of the coil construction in providing a receiver coil. This may also be particularly advantageous where the transmitter coil is provided as part of a wearable garment, e.g. a vest or a pair of shorts comprising one or more of the flexible transmitter coils. The coil construction may therefore be additionally or alternatively applied to a transmitter coil. An apparatus may comprise receiver and/or transmitter coils according to this advantageous construction.

In some embodiments at least some, or the or each transmitter coil of the external transmitter apparatus is attached to one or more wearable garment. The or each garment and its transmitter coil(s) provides a coil unit for the external transmitter unit. Where multiple coils are provided, each coil may be attached to the same garment, or different coils e.g. pairs of coils, may be attached to different garments. Each coil is attached to a given garment. For example a pair of coils may be attached to a vest type garment, and a pair of coils to a short type garment. From a further aspect the present invention provides a transmitter coil unit for an external transmitter apparatus for use with an implantable receiver apparatus connected to a medical device, the transmitter coil unit comprising a wearable garment having one or more transmitter coils attached thereto, wherein each of the flexible transmitter coils comprises at least one coil layer comprising a coil portion printed on a flexible substrate. It will be appreciated that the present invention in accordance with the further aspect may include any or all of the features described in relation to any of the embodiments of the earlier aspects of the invention to the extent they are not mutually inconsistent therewith, and vice versa.

In these further aspects and embodiments, the coil unit may be disposable. The or each transmitter coil may be arranged to be connected to another part of the external apparatus for causing the coil to transmit i.e. transcutaneously to a receiver coil of the implantable receiver apparatus in use. The other part of the external apparatus may comprise power supply means or pulse generation means. The connection may be a releasable connection to permit the coil unit to be replaced by a new coil unit. There may be a plurality of transmitter coils attached to the garment e.g. a given number of pairs of coils. The transmitter coil(s) may be permanently or releasably attached to the garment. A permanent connection may be suitable for disposable garments. In these further aspects or embodiments, the flexible transmitter coils and/or the external transmitter apparatus may be in accordance with any of the embodiments herein described herein i.e. relating to the construction of the coils. The garment may be in accordance with any of the embodiments described in relation to the earlier aspects.

From a further aspect of the invention there is provided an external transmitter apparatus for a TET system, the external transmitter apparatus comprising one or more flexible transmitter coil, each transmitter coil being arranged to transmit power to a receiver coil of an implantable receiver apparatus of the TET system when in proximity thereto in use for supplying power to an implantable medical device connected to the implantable apparatus, wherein each of the flexible transmitter coils of the external transmitter apparatus comprises at least one coil layer comprising a coil portion printed on a flexible substrate.

It will be appreciated that the present invention in accordance with the further aspect may include any or all of the features described in relation to any of the embodiments of the earlier aspects of the invention to the extent they are not mutually inconsistent therewith, and vice versa.

The present invention in this further aspect extends to a TET system comprising the external transmitter apparatus and an implantable receiver apparatus connected to a medical device, and comprising one or more receiver coils, each being arranged to receive power from a respective transmitter coil of the external transmitter apparatus. The power transmission may be continuous or pulsed.

From a further aspect of the invention there is provided an external transmitter apparatus for use with an implantable receiver apparatus connected to a medical device, the external transmitter apparatus comprising one or more flexible transmitter coil, each transmitter coil being arranged to provide a transmission to a receiver coil of the implantable receiver apparatus when in proximity thereto in use, wherein each of the flexible transmitter coils of the external transmitter apparatus comprises at least one coil layer comprising a coil portion printed on a flexible substrate.

It will be appreciated that the present invention in accordance with the further aspect may include any or all of the features described in relation to any of the embodiments of the earlier aspects of the invention to the extent they are not mutually inconsistent therewith, and vice versa.

The present invention extends to the use of the external transmitter apparatus of the invention in these further aspects or embodiments, and to such an apparatus mounted to the body. The method may comprise the or each transmitter coil of the apparatus providing a transmission to a receiver coil of an implantable apparatus.

Again, in these aspects relating to transmitter coils, the transmission is transcutaneous i.e. wireless.

The external transmitter apparatus in any of these aspects may comprise one or more wearable garment to each of which garment(s) one or more of the flexible transmitter coils are mounted. Thus, preferably at least some of the transmitter coils are mounted to a garment or garments which may be worn by a user. The or each garment may be of any of the forms described above, e.g. the garment may be a woven or non woven garment, and may be disposable. The or a garment may be adapted to be worn around the chest and/or the abdomen. The or a garment may be a vest or shorts.

From a yet further aspect, the present invention may provide a wearable garment comprising at least some of the coils of an external transmitter apparatus substantially as described or below above and/or including any or all of the features described in relation to any of the embodiments of the earlier or later aspects of the invention to the extent they are not mutually inconsistent therewith and vice versa. In particular, by providing one or more flexible transmitter coils as part of a wearable garment, the transmitter coils may be held relatively securely in position relative to the wearer's body. The wearable garment may comprise at least a pair of the transmitter coils. In some embodiments, a set of a plurality of wearable garments may be provided, each comprising at least some of the transmitter coils of the external apparatus e.g. respective pairs thereof. The garment(s) may be adapted to be worn about the chest and/or abdomen of a wearer e.g. being a vest and/or shorts. As described in relation to the earlier aspects, the other components of the external transmitter apparatus may or may not be mounted to the garment, or a one of a set of garments, having the coil(s) thereon. For example, at least some of the other components of the apparatus may be mounted to a belt.

It will be appreciated that the present invention in accordance with the further aspect may include any or all of the features described in relation to any of the embodiments of the earlier aspects of the invention to the extent they are not mutually inconsistent therewith, and vice versa.

Whether or not it includes a wearable garment, the invention may extend to a system comprising the external transmitter apparatus in any of its aspects or embodiments having one or more flexible transmitter coil, and an implantable receiver apparatus comprising one or more receiver coil for receiving a transmission from at least some of the one or more transmitter coils of the external transmitter apparatus. The method may comprise operating a transmitter coil or coils of the external transmitter apparatus to provide a transmission that is received by a receiver coil of the receiver apparatus. Of course, in aspects or embodiments of the invention including both the external transmitter apparatus and an implantable receiver apparatus, the transmitter coil(s) of the external transmitter apparatus and the receiver coil(s) of the implantable receiver apparatus may both be of the advantageous flexible construction. The transmission is transcutaneous i.e. wireless.

The transmission in these further aspects or embodiments of the invention preferably comprises an RF pulse.

References to the implantable apparatus being connected to an implantable medical device encompass the apparatus being attached to a separate medical device e.g. where it is an implantable apparatus of a TET system, or forming part of a medical device e.g. a defibrillator.

In some embodiments the external transmitter apparatus is an external transmitter apparatus of a TET system, and each transmitter coil is arranged to transmit power to a receiver coil of an implantable receiver apparatus of the TET system when in proximity thereto in use for use in energising an implantable medical device connected to the implantable receiver apparatus. In preferred embodiments the apparatus then comprises a plurality of the flexible transmitter coils. Each transmitter coil may be arranged transmit power to a given one of a plurality of receiver coils of the implantable receiver apparatus. The present invention in this further aspect extends to a TET system comprising the external transmitter apparatus and further comprising an implantable receiver apparatus comprising one or more receiver coils for receiving power from the at least one transmitter coil of the external transmitter apparatus. The power transmission may be continuous or pulsed.

It will be appreciated that the present invention in accordance with the further aspect may include any or all of the features described in relation to any of the embodiments of the earlier aspects of the invention to the extent they are not mutually inconsistent therewith, and vice versa.

In other embodiments the external transmitter apparatus is an external transmitter apparatus of a pulse delivery apparatus, wherein the external transmitter apparatus is arranged to transmit a RF pulse transcutaneously to an implantable receiver apparatus of the pulse delivery apparatus in use for use in applying a pulse to implantable electrodes connected to the implantable receiver apparatus to enable a pulse to be delivered to the body when the electrodes are implanted in a part of the body in use. In this context a single transmitter coil may be provided, or multiple transmitter coils may be present. In preferred embodiments the pulse delivery apparatus is a cardiac defibrillator apparatus, and the external transmitter apparatus is arranged to provide an RF pulse for use in applying a defibrillator pulse to implantable electrodes connected to an implantable receiver apparatus of the cardiac defibrillator apparatus to enable a pulse to be delivered to the heart when the electrodes are implanted in the heart in use. The cardiac defibrillator may be a passive implantable atrioverter defibrillator (PIAD). However, the pulse delivery apparatus may be an apparatus used in delivery a pulse to other parts of the body, such as the brain.

The present invention extends to a pulse delivery apparatus e.g. a cardiac defibrillator apparatus comprising the external transmitter apparatus having one or more flexible transmitter coils of these further aspects of the invention and an implantable receiver apparatus arranged to receive a RF pulse transmitted transcutaneously by the external transmitter apparatus of the pulse delivery apparatus in use and to use the received RF pulse in applying a pulse to implantable electrodes connected to the implantable receiver apparatus to enable a pulse to be delivered to the body when the electrodes are implanted in a part of the body.

It will be appreciated that the present invention in accordance with the further aspect may include any or all of the features described in relation to any of the embodiments of the earlier aspects of the invention to the extent they are not mutually inconsistent therewith, and vice versa.

The present invention extends to a method of manufacturing the external transmitter apparatus of any of the aspects or embodiments of the invention having one or more flexible transmitter coils comprising at least one coil layer having a coil portion printed on a substrate, the method comprising the step of printing the or each coil portion on a respective flexible substrate.

It will be appreciated that the present invention in accordance with the further aspect may include any or all of the features described in relation to any of the embodiments of the earlier aspects of the invention to the extent they are not mutually inconsistent therewith, and vice versa.

In any of the aspects of the invention relating to an external transmitter apparatus having one or more flexible coils, the or each coil may be attached to a wearable garment as earlier described. Different coils may be attached to the same or different wearable garments. Each wearable garment and its flexible coil(s) provide a coil unit of the external transmitter apparatus. The or each transmitter coil may be releaseably connected to another part of the external apparatus for causing the coil to transmit to a receiver coil of the implantable receiver apparatus in use.

The term "receiver coil" in the further aspects or embodiments referring to a flexible receiver coil construction refers to a coil which is arranged to perform a receiving function. The coil may be arranged only to receive, or may be arranged to both receive and transmit. In some embodiments the coil is arranged solely to receive. The term "transmitter coil" in these further aspects or embodiments referring to a flexible transmitter coil construction refers to a coil which is arranged to perform a transmitting function. The coil may be arranged only to transmit, or may be arranged to both receive and transmit. In some embodiments the coil is arranged solely to transmit.

In accordance with any of the aspects or embodiments of the invention relating to an implantable receiver apparatus or an external transmitter apparatus (or to a system or method involving such an apparatus) having one or more coils, each of which comprises at least one coil layer comprising a coil portion printed on a flexible substrate layer, each coil is flexible. Each coil of the apparatus is preferably of this flexible construction. There may be a single receiver or transmitter coil, or a plurality of such coils. Where a plurality of transmitter or receiver coils are provided, each is preferably independently positionable. Thus the coils are preferably not physically connected to one another. A coil layer refers to a layer in the final receiver coil construction e.g. a layer of a laminate where multiple layers are present. Multiple coil layers may be formed by folding a single substrate layer during manufacture of the coil, or by joining discrete substrate layers to one another, or by combinations thereof.

The above and following features are applicable to a flexible receiver coil or a flexible transmitter coil used in accordance with any of the aspects and embodiments of the invention involving such flexible coils.

Each flexible coil is preferably substantially planar.

A coil may be formed from one or more coil layers. Preferably each coil layer includes only a single coil portion. Preferably a coil portion is printed on only one side of the or each coil layer. However, alternatively, coil portions may be printed on both sides of at least some of the coil layers.

In preferred embodiments, each coil is formed from a plurality of coil layers, and most preferably from an even number of coil layers, such as two or four coil layers. Preferably the coil is of a laminate construction, comprising a plurality of coil layers. Preferably the coil portions are provided to the interior of the laminate and the external surfaces of the coil laminate are free from printed coil portions. The coil layers here refer to the layers of the final coil construction i.e. which is used. In other embodiments the or a coil portion may be printed on a or both external surfaces of the coil laminate. In this case, the coil portions may be provided with an insulating coating layer.

In some preferred embodiments a coil comprises at least one pair of coil layers, each coil layer of the pair having a coil portion printed on only one side of the substrate layer thereof, wherein the coil layers of the pair are fixed to one another with the sides of the substrate layers having the coil portions thereon to the interior of the resulting laminate. In other words, the coil portions are sandwiched together to the interior of the laminate. The outer surfaces of the laminate are provided by the reverse sides of the respective substrate layers. The reverse side of a substrate layer refers to the side opposite that having the coil portion i.e. the side that is free from any coil portion.

The coil may comprise a plurality of such pairs of coil layers fixed to one another. Each pair of coil layers may then provide a sub-assembly for the coil. In some embodiments the coil comprises two such pairs of coil layers. The coil layers may be fixed to one another by adjacent reverse sides of the respective substrate layers. Of course, other arrangements may be used. The method may comprise providing at least first and second coil sub-assemblies and attaching them to one another.

The coil portions printed on each substrate layer of a multi-layer coil are electrically connected to one another to enable them to act as a single coil. The coil portions are connected in series. This may effectively increase the number of turns of the coil, without increasing the surface area thereof. Where a coil comprises multiple coil portions, preferably each coil portion is of identical construction.

Each coil portion is substantially planar.

The final coil may comprise or consist of a plurality of separately formed discrete coil layers which are attached together. Each of the coil layers of the coil may be a separately formed discrete coil layer. In other embodiments the (final) coil may comprise or consist of a plurality of coil layers which are defined by folding a substrate layer having multiple e.g. a pair of coil portions thereon to provide a plurality of coil layers, each having a coil portion thereon. The substrate may be secured in the folded form. Each coil layer of the coil may be provided by a single common substrate in this way. A coil may comprise a mixture of separately formed coil layers, and layers formed through folding a common layer.

A first set of multiple coil portions e.g. a pair of coil portions may be printed on a first substrate layer common to the coil portions, with the substrate layer being folded to provide a plurality of coil layers, each comprising a respective one of the coil portions. In some embodiments, prior to folding the first substrate layer, a further set of multiple coil portions e.g. a pair of coil portions may be printed on to a further substrate layer common to the further set of multiple coil portions, and the further substrate layer having its further set of multiple coil portions is fixed to the first substrate layer having the first set of coil portions thereon to provide at least first and second coil sub-assemblies, each comprising an opposed pair of coil portions, and the laminate of the first and further substrate layers having the coil portions thereon folded between the or each sub-assembly to provide a coil having at least four coil layers, each with a respective coil portion thereon. Thus the first substrate layer is folded at the same time as the further substrate layer. Arrangements comprising any even number N of coil layers, wherein N is greater than or equal to four, may be made in this way, but providing N/2 coil-subassemblies. Of course, a multi e.g. four layer coil may alternatively be constructed using a corresponding number of separately fabricated, discrete coil layers. The method of manufacturing the coil may include such steps.

In one exemplary arrangement, a method of constructing a coil (whether a transmitter or a receiver coil) may comprise; printing a first pair of coil portions side by side and spaced apart on a surface of a first substrate layer, printing a second pair of coil portions on a surface of a second substrate layer, fixing the first and second substrate layers to one another with the first and second pairs of coils one above the other and facing one another to the interior of the resulting laminate, opposed ones of the first and second pairs of coils providing first and second sub-assemblies for the coil, and folding the laminate along a line separating the coils of the first and second sub-assemblies to provide a coil including four coil layers. The method may comprise fixing the folded laminate in the folded configuration.

However many coil layers are present, and whatever the construction of the coil, where a coil comprises multiple coil layers, preferably the substrates of the coil layers are fixed to one another in the coil only at a periphery of the substrate and at a centre thereof. The fixing may be through adhesive, and/or through a folded edge. This relates to the fixing of the substrates in the final, assembled coil. This may ensure that the resulting coil maintains suitable flexibility properties. Preferably the coil layers are joined together with the printed coil portions to the interior of the coil i.e. to the interior of the laminate defined where the coil comprises a plurality of coil layers. The coil portions will then be insulated from the exterior environment by the reverse side of the outermost substrate layers. Where the coil comprises two or more sets of a pair of coil portions, each pair of coil portions may be disposed in face to face relationship with one another with a substrate layer separating each the pair of coils from an adjacent pair of coils.

The following features are applicable to the or each coil layer of a coil. The coil portion is printed on the substrate. This is in contrast to a coil which is mechanically wound e.g. on a mandrel. The coil layer is substantially planar. The coil portion may be printed on to the substrate by adding conductive material to the surface, or removing conductive material from a conductive layer provided on the surface, or combinations thereof, to result in a pattern of conductive material being provided on the surface of the substrate defining the coil portion. By way of example only, the coil portion of a coil layer may be printed using any one or ones of the following techniques; laser milling, photolithography, ink-jet printing.

In some embodiments a film layer of conductive material is deposited on to the substrate and patterned during or after deposition using one of the above techniques to provide the coil portion. The film layer may be a thin film layer having a thickness in the range of from 5 µm to 30 µm. The deposition of the thin film layer may be carried out using techniques such as RF sputtering, thermal evaporation, e-beam deposition or ion beam techniques. Patterning may be carried out using photolithography e.g. photo-resist based photolithography, or laser milling e.g. 3D laser milling, or masking during deposition e.g. shadow masking. In other embodiments the film layer may be provided by a conductive ink deposited on the substrate, preferably wherein the conductive ink comprises a powder e.g. a metallic powder. Such a film layer may provide a so-called "thick film". Whatever the nature of the deposited film layer, the method preferably further comprises heating the patterned film layer, preferably to a temperature of between 100 degrees Celsius and 300 degrees Celsius. This may act to sinter a powder, when a conductive ink comprising a powder is used, or otherwise bake the deposited film layer. The heating is preferably performed to obtain a conductivity of the deposited material in the range of from 5 to 30 µΩ/cm.

The substrate may be of any suitable type that is suitably flexible to conform to the skin of the user e.g. around the chest wall, is skin compatible, and has an appropriate level of thermal stability. For example, silicone or polytetrafluoroethylene (PTFE) may be used. Preferably the substrate is a polyimide substrate. Polyimide is particularly suitable, as it has a high level of thermal stability, and good electrical isolation, flexibility and biocompatibility properties.

The coil portion may be printed on to a disc of the substrate.

The conductive material that defines the coil portion may be any suitable material. The conductive material is preferably a metallic material. Gold, platinum, silver and alloys thereof have been found to be particularly advantageous. The conductive material may therefore comprise gold, platinum, silver, or an alloy of one or more of gold, platinum and silver. These materials have low resistivity properties and good levels of biocompatibility.

A given coil portion may comprise any number of turns (N), where N is greater than or equal to 2. Preferably each coil portion is a spiral coil portion. A spiral coil portion comprises multiple turns of increasing radius. The turns are coaxial. Each turn is about an axis extending through a radial centre of the coil portion. Preferably the spiral coil portion is an elliptical spiral coil portion. However, the coil portion may be of other shapes, such as circular, rectangular, square etc. Each turn of the coil portion is of the shape mentioned.

The number of turns of each transmitter or receiver coil may be selected as desired.

The outer contour of the or each coil is preferably rounded. This provided greater comfort to a user. The outer contour of the or each coil is preferably disc shaped. The contour of the or each coil is preferably elliptical. Of course coils of other shapes may be used. For example, the outer contour may be circular. The outer contour of a coil is defined by the outer contour of the substrate of the or each coil layer thereof. Preferably each coil layer is of the same shape and size. The edges of the coil layers are preferably flush with one another.

The following dimensions refer to the coil as a whole, i.e. including all constituent layers thereof. Preferably each coil has a maximum diameter of no greater than 60 mm, or 55 mm, or most preferably 50 mm. The coil may have a minimum diameter of at least 30 mm, or 35 mm, or preferably 40 mm. In the case of a circular coil, the minimum and maximum diameters will be the same. In the case of an elliptical coil, the minimum and maximum diameters will differ. These dimensions are similar to those of an implantable pacemaker e.g. an ellipse of around 40 mm×50 mm. Where the coil comprises one or more coil layer including a coil portion printed on a substrate, the diameter of the substrate and the coil portion may both be within this range. Each substrate layer of the coil is preferably similar in area to the coil printed thereon, to provide a space efficient arrangement.

Preferably each coil has a total thickness in the range of from 0.2 to 1.5 mm. The total thickness of the coil refers to the thickness from the upper surface to the lower surface, including all coil layers present. Thus, where coil is a composite coil comprising multiple coil layers, the composite coil has a thickness in this range.

Where the coil is a receiver coil, each receiver coil is preferably connected to a proximal end of a flexible lead for transporting a transmission e.g. signal received by the coil away from the coil. The lead may have any suitable length, depending upon the size of the intended wearer. The flexible lead may, for example, have a length in the region of from 15 cm to 80 cm. The most appropriate length will depend upon the application and the size of the user and the intended position of the receiver coil. The lead may have one or more terminals or electrodes at the distal end thereof for transmitting a transmission e.g. signal received from a transmitter coil for use by the implantable device. In embodiments in which the receiver coil forms part of an implantable receiver apparatus of a pulse delivery apparatus e.g. a cardiac defibrillator apparatus, the lead may be used to transmit an RF pulse to a part of the body e.g. the heart. The lead may then have one or more electrodes at the distal end thereof, and may terminate in an electrode.

In use, the or each electrode is implanted in the body e.g. the heart. In embodiments in which the receiver coil forms part of an implantable apparatus of a TET system, the lead may be used as described in any of the earlier aspects or embodiments of the invention relating to transport of received power away from the coil. The lead may deliver power to a power management system of the TET system. The lead may have one or more output terminals e.g. for connection to a power management system.

Where the coil is a receiver coil, preferably each receiver coil is connected to a tuning capacitor arrangement for tuning the resonant frequency of the receiver coil circuit. The resonant frequency of a receiver coil circuit is preferably selected based on the operating frequency of a transmitter coil circuit with which the receiver coil communicates. The resonant frequency of the receiver coil circuit may also depend upon the number of turns of the coil. Where the coil is a receiver coil connected to a flexible lead as described above, preferably the tuning capacitor arrangement forms part of the lead e.g. at a proximal end thereof. The tuning capacitor arrangement is preferably provided as a flexible strip which is integrated into the lead. The transmission e.g. signal received by a receiver coil or transmitted by a transmitter coil may be pulsed, such as a pulse of a pulsed power supply or a defibrillating pulse. An implantable receiver apparatus may be arranged to carry out some processing e.g. rectification and/or filtering of a transmission received by the receiver coil e.g. to obtain a pulse suitable for use by the implantable medical device.

In some embodiments relating to an implantable receiver apparatus having one or more flexible receiver coil, the implantable receiver apparatus comprises rectification means for rectifying a transmission e.g. signal received by the or each receiver coil. The rectifying means may be any suitable circuitry e.g. comprising a set of one or more diodes. Rectifying means is preferably provided in respect of each receiver coil. The rectifying means may convert received AC pulses of the power supply into DC pulses. The receiver apparatus may further comprise means for filtering e.g. smoothing an output of the rectifying means. The filtering means is preferably passive filtering means i.e. that does not include any active components. Filtering circuitry may be provided in respect of the rectifying means for each coil.

In preferred embodiments in which each receiver coil of the implantable receiver apparatus is connected to a respective flexible lead, preferably rectifying and/or filtering means for the coil, and preferably both rectifying and filtering means, is associated with each flexible lead. The components of the rectifying and/or filtering means, and preferably of both the rectifying and filtering means, are preferably distributed along the length of the lead. The rectifying and filtering means may be distributed along respective portions of the length of the lead. The components should be provided in such a manner that maintains a flexibility of the lead. The flexible power delivery lead may have a proximal end and a distal end, the proximal end being connected to the receiver coil, wherein the rectifying means is preferably provided by a set of diodes distributed along a proximal portion of the lead. The filtering means, where present, is provided distal to the rectifying means. The rectifying means may be associated with a first proximal portion of the length of the lead, and the filtering means with a second portion of the length of the lead distal thereto. The first portion may be of greater diameter than the second portion. The rectifying means may be distributed along the length of the first portion, and the filtering means along the length of the second portion. The second portion may not extend to the distal end of the lead. The filtering means may be provided by a set of parallel capacitors, such as a flexible strip of capacitors attached to the lead, or may be integral with the lead. For example, the filtering means may be provided by a length of coaxial cable forming part of the lead e.g. defining a second portion thereof. Of course, rather than providing rectifying and/or filtering means as part of the lead, a distal end of the lead may, in use, be connected to such means. In such cases, any suitable material may be used for the lead taking into account its intended application.

The lead may comprise a flexible outer sheath, such as a polyurethane sheath.

In embodiments in which the coil is a transmitter coil, each transmitter coil may be connected to a tuning capacitor arrangement for tuning the resonant frequency of the transmitter coil circuit. The resonant frequency of the transmitter coil circuit is preferably selected based on the operating frequency of a receiver coil circuit with which the transmitter coil communicates. The term "RF pulse" ("radio frequency pulse") refers to a burst of alternating current (AC) radio frequency signal. The pulse is typically of a relatively short duration, such as a few milliseconds. A pulsed power supply comprises a series of such pulses.

It will be appreciated that references to a "coil" herein refer to a complete coil assembly including its associated electrical connection terminals. A coil may also be known as an inductor L which may have a particular inductance value (in Henrys H).

The methods in accordance with the present invention may be implemented at least partially using software e.g. computer programs. It will thus be seen that when viewed from further aspects the present invention provides computer software specifically adapted to carry out the methods herein described when installed on one or more data processors, a computer program element comprising computer software code portions for performing the methods herein described when the program element is run on one or more data processors, and a computer program comprising code adapted to perform all the steps of a method or of the methods herein described when the program is run on a data processing system. The one or more data processors may be a microprocessor system, a programmable FPGA (field programmable gate array), etc.

It will be appreciated that the apparatus and techniques described herein in relation to the invention in its various aspects or embodiments may also find general applicability in other fields where wireless power transmission may be required e.g. in transport or telecommunications. A skilled person will understand how, and which aspects of, the invention may be extended to applications other than for supplying power transcutaneously to implantable medical devices.

Thus, in accordance with a further aspect of the invention there is provided an external transmitter apparatus for a wireless energy transfer system for supplying power for use in energising a device or system in use, the external transmitter apparatus comprising:

a plurality of transmitter coils, each transmitter coil being capable of transmitting power wirelessly to a respective one of a plurality of receiver coils of a receiver apparatus of the system when located in proximity thereto in use for use in energising a device or system connected to the receiver apparatus in use, the external transmitter apparatus for the system further comprising power supply means for providing a pulsed power supply to each one of the transmitter coils of the external transmitter apparatus in use for transmission wirelessly by the transmitter coil to a respective receiver coil of the receiver apparatus when located in proximity thereto, wherein each transmitter coil is associated with a respective power supply channel, and the power supply means is arranged to deliver the pulsed power supply to each transmitter coil over the respective power supply channel associated therewith.

The invention may also provide a wireless power transmission system comprising the external transmitter apparatus of this further aspect, and a receiver apparatus connected to a device or system for supplying power wirelessly thereto. The invention may also provide methods of operating the external transmitter apparatus and system, the methods comprising using the power supply means to provide a pulsed power supply to each one of at least some of the plurality of transmitter coils of the external transmitter apparatus.

The present invention also extends to a kit of parts for the external transmitter apparatus, or implantable receiver apparatus, or TET system or pulse delivery system of the invention in any of its aspects or embodiments. A kit of parts for an external transmitter apparatus, whether or not forming part of a system, may comprise one or more coil unit e.g. one or more wearable garments, each having one or more transmitter coils attached thereto. For external transmitter apparatus for a TET system, the apparatus may further comprise power supply means.

Where not explicitly stated, it will be appreciated that the invention in any of its aspects may include any or all of the features described in respect of other aspects or embodiments of the invention to the extent they are not mutually exclusive. In particular, while various embodiments of operations have been described which may be performed in the method and by the system or apparatus, it will be appreciated that any one or more or all of these operations may be performed in the method and by the system or apparatus, in any combination, as desired, and as appropriate.

BRIEF DESCRIPTION OF THE DRAWINGS

Some preferred embodiments of the invention will now be described by way of example only and with reference to the accompanying drawings of which:

FIG. 7b is a longitudinal cross sectional view through the coil and flexible lead of FIG. 7a;

FIG. 11 illustrates the results of preliminary bench test evaluation of the DC to DC energy transfer obtained using a TET system in accordance with embodiments of the invention;

DETAILED DESCRIPTION OF THE PREFERRED EMBODIMENTS

A first embodiment of the invention will now be described.

Figure 1:
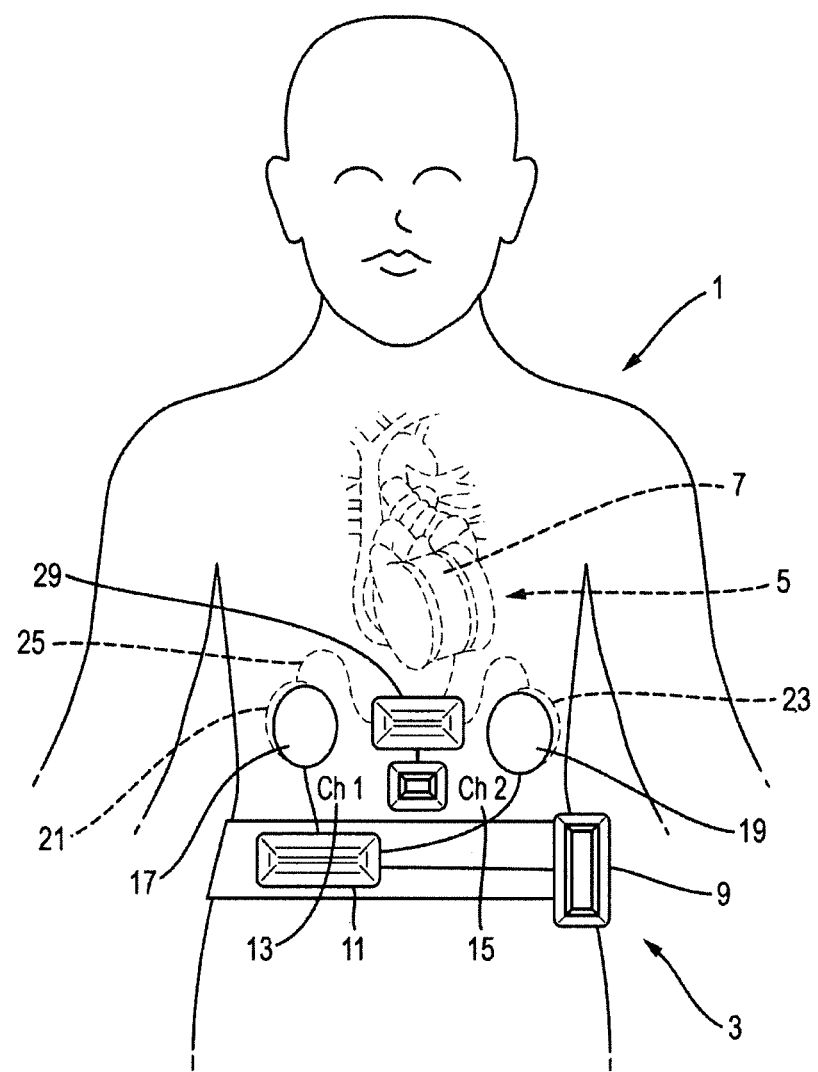
FIG. 1 illustrates a TET system disposed in an "in use" configuration with respect to a user in accordance with an embodiment of the invention.

FIG. 1 illustrates schematically the components of a TET system 1 in accordance with an embodiment of the invention disposed in an "in use" configuration with respect to a user. The TET system includes an external transmitter apparatus 3 and an implanted receiver apparatus 5, which is connected to an artificial heart pump 7, such as a left ventricular assist device (LVAD).

The external transmitter apparatus 3 of the TET system includes a power supply system including an external rechargeable battery 9, and a power supply unit 11 for generating a pulsed power supply for delivery over two channels 13, 15 (which may be referred to as Ch1 and Ch2). The battery 9 may be a lithium ion battery. The power supply unit 11 may comprise an energy storage means common to each of the channels comprising a capacitor, with a switching arrangement e.g. a switching transistor or transistors being provided for generating the RF pulses on each channel. Each channel may comprise a separate, dedicated switching arrangement. The capacitor may be a large storage capacitor with a positive common node. The or each switching transistor may be an RF power switching transistor. It will be appreciated however that other means of providing RF pulses to the different channels may suitably be used with the present invention. The channels are defined by respective wires. Each channel 13, 15 is connected to a respective one of a pair of transmitter coils 17, 19. The transmitter coils 17, 19 may be any suitable such coils used in the art, and may, for example be standard primary spiral copper coils, or may be of the advantageous new construction described below. The transmitter coils 17, 19 are secured (e.g. adhesively) to the exterior of the skin of the user at two different locations, in alignment with respective ones of a pair of receiver coils 21, 23 associated with the implantable receiver apparatus of the TET system, and disposed on the interior of the skin of the user i.e. on the chest wall. The pairs of opposed transmitter and receiver coils are arranged to couple to one another through the skin of the user when an RF pulse is applied to the external transmitter coil, to enable power to be transmitted to the implanted apparatus. The power supply unit 11 and the external rechargeable battery 9 are mounted to a belt 10 which is worn by the user.

Turning to the implanted receiver apparatus of the TET system, the receiver coils 21, 23 are connected via respective power delivery leads 25, 27 to a power management system 29, which is connected via a wire to the artificial heart pump 7. The power management system 29 is also connected via a wire to a rechargeable backup battery 31 for the heart pump. The battery may be a lithium ion battery.

Figure 2:
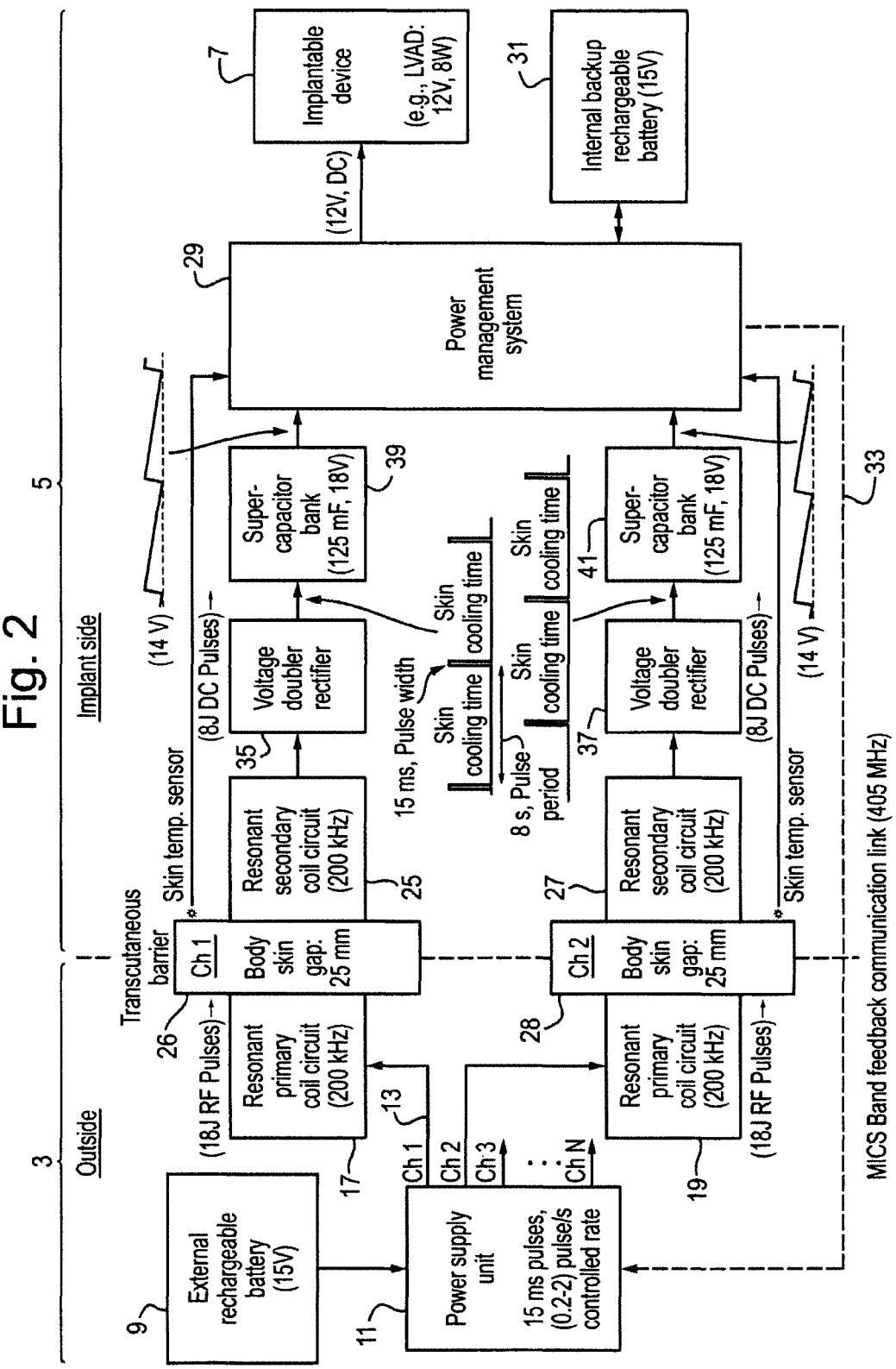
FIG. 2 is a block diagram illustrating the components of the TET system.

FIG. 2 is a block diagram illustrating the way in which the components of a system such as that shown in FIG. 1 interact with one another in more detail, and illustrating certain further features of the system which are not shown in FIG. 1. The external transmitter and implanted receiver parts 3, 5 of the TET system are indicated, and are used to deliver power to the implanted device 7 and the internal backup rechargeable battery 31. FIG. 2 includes some exemplary operating parameters for the components of the system. It will be appreciated that these are by way of example only.

The external rechargeable battery 9, which, in the exemplary embodiment, is a 15V lithium ion rechargeable battery, is arranged to provide power to the power supply unit 11. The power supply unit 11 is arranged to generate RF pulses on a plurality of different channels, channels 1 ... N as shown in FIG. 2. In the illustrated embodiment, only channels 1 and 2 are used, being connected to the two transmitter coils 17 and 19 respectively. However, in arrangements with a greater number of transmitter coils, more than two channels may be used. Each channel will be associated with the delivery of power through a different area of the skin of the user, corresponding to the position of the transmitter coil associated with the channel. Suitably, the transmitter coils may be positioned around the waist in the abdominal area and/or on the upper right and left chest walls of the user e.g. with a pair of coils at the abdomen and a pair on the chest. Any further transmitter coil will located in alignment with a further receiver coil of the implanted apparatus, such that each transmitter coil forms part of a transmitter-receiver coil pair. It has been found that up to 4 channels may be particularly suitable.

The transmitter coils 17, 19 each form part of a tuned circuit, such that they each have a resonant frequency corresponding to the frequency of the RF pulses applied thereto by the power supply unit 11 via the respective channels 1 and 2. The resonant frequency is preferably in the range of from 100-300 kHz, although operation at frequencies outside this range is not excluded. In the exemplary embodiment, all of the channels are tuned to transmit at the same frequency and the frequency of the RF pulses applied on each channel i.e. the resonant frequency of each of the transmitter coils is 200 kHz.

The power supply unit 11 is arranged to deliver RF pulses at a rate of from 0.03-10 pulses per second on each of the channels. Each pulse has a duration, in this example, of 15 ms. On each channel, there is an interval between pulses in which no pulse, and hence RF energy, is applied. The timing of the pulses delivered on each channel is controlled such that the pulses do not overlap. In other words, a pulse on one channel is delivered in a gap between pulses on the other channel. In this example, each pulse delivers 18 J. If there are more than two channels used, the timing of the delivery of pulses on the additional channels is controlled similarly, such that the pulses applied to any of the channels do not overlap, and energy i.e. a pulse is delivered via only one channel at a time.

As shown in FIG. 2, the transmitter coils couple to their respective receiver coils through the skin interface, which is around 25 mm in thickness. The two channels provide first and second channels for delivering power to the implanted receiver apparatus. The receiver coils 25, 27 also form part of respective tuned circuits, such that they each have a resonant frequency of 200 kHz, corresponding to the resonant frequency of the transmitter coils, and the RF frequency of the applied pulses. The receiver coils 25, 27 may be any type of secondary coil known in the art. However, the Applicant has found that further advantages may be associated with using a particular coil construction which has been developed, and will be described in more detail below. The RF pulses applied to the transmitter coils induce corresponding pulses in the receiver coils. The RF pulses received by each receiver coil are subjected to rectification to convert them to DC pulses. In FIG. 2, a voltage doubler rectifier 35, 37 is provided for this purpose in respect of each of the receiver coils associated with the first and second channels respectively. In the example of FIG. 2, this results in 8 J DC pulses. As schematically shown in FIG. 2, the pulses obtained in respect of the first and second channels, which each have a duration of 15 ms, are separated by a certain time interval, which is relatively long in comparison to the duration of the pulse. Furthermore, it may be seen that the pulses received by channel 2 occur in the intervals between the pulses received over channel 1. This is as a result of the timing and duration of the RF pulses delivered by the power supply unit 11 over the two channels.

The DC pulses obtained via the receiver coils associated with channels 1 and 2 respectively are delivered to supercapacitor banks 39, 41 associated with the respective channels. The supercapacitor banks each provide an overall capacitance of 125 mF and have a voltage rating of 18V. Each pulse received by the supercapacitor bank serves to recharge the supercapacitors. The voltage provided by each supercapacitor bank is schematically illustrated in FIG. 2. It may be seen that the voltage gradually decreases as the supercapacitors discharge, before increasing again as they are charged by the next pulse. In this way the discharge voltage of the supercapacitor banks 39, 41 (i.e. their voltage outputs) may be sustained above a certain minimum voltage threshold. The rate of pulse delivery is controlled so as to sustain the voltage output above the voltage (or power) rating of the implantable medical device (e.g. 6V for an LVAD device). Thus, a continuous supply of power/voltage may be provided to the implantable medical device. The voltage provided by the supercapacitors is provided to the power management system 29, which combines the power received over the two channels, and directs it to the implantable device 7 and/or the internal back up rechargeable battery 31 respectively as required. The supercapacitor banks may alternatively be located in a housing of the power management system 29. The internal battery is a 15V lithium ion battery in this example. The implantable device 7 is a higher power rated implantable medical device, such as an LVAD, in this example having a power rating of 8 W, and requiring a 12 V DC power supply. The internal backup battery 31 is used to power the implantable device when insufficient power is received from the external transmitter apparatus of the TET system, e.g. when this is disconnected by the user, when washing, or if there is an interruption in the power supplied from the external transmitter apparatus for any other reason, such as a problem with the coupling between the transmitter-receiver coils.

Although FIG. 2 illustrates the case where separate supercapacitor banks 39, 40 are provided in respect of each of the two channels, it will be appreciated that in other embodiments the two channels may share a common supercapacitor bank such that the pulses provided on each channel act to recharge the same supercapacitor bank. This arrangement may be advantageous in some contexts in that using a single common supercapacitor bank may be more efficient and more compact than providing a plurality of supercapacitor banks associated with each of the plurality of channels.

The power management system 29 is arranged to control the delivery of power to the implantable device and/or the internal backup rechargeable battery, to regulate the voltage of the power supplied, and also to provide feedback to the external transmitter apparatus of the TET system. It will be appreciated that the power management system 29 may simultaneously deliver power to the implanted device and the backup battery. Where power is simultaneously delivered to the implanted device and the backup battery, the power supply to the implanted device will generally take priority. For example, in a two-channel system where one channel has entered into a fault state, a single channel will supply power to both the medical device, at top priority, but also charge the battery (at a very slow speed) until the fault is resolved. The power management system 29 may direct energy received over one channel to the implanted device and energy received over the other channel to the backup battery. Internal skin temperature sensors 26, 28 are provided on the interior of the skin, and are arranged to measure the internal temperature of the skin in the region of the two receiver coils 17, 19. The sensors provided sensed temperature data to the power management system 29. The power management system 29 is arranged to provide sensed temperature data via a wireless feedback communication link 33 to the power supply unit 11 of the external transmitter apparatus for use in controlling the delivery of pulses over the plurality of channels. The communication link operates at a frequency of 405 MHz in the example, which is within the Medical Implant Communication Service (MICS) frequency band. Other data relating to the operation of the implanted medical device (e.g. for an LVAD device, a blood pumping volume), the state of the internal rechargeable backup battery (e.g. a battery charge level, or whether the battery is undergoing charging), or data indicative of faults or malfunction (including e.g. improper positioning of the external transmitter coil) may also be provided from appropriate sensors or monitoring arrangements (not shown) e.g. associated with the power management system over the feedback link for use by the external power supply unit 11 in controlling the delivery of energy over the channels.

It will be appreciated that the operating parameters of the system shown in FIG. 2 are by way of example only.

Figure 3:
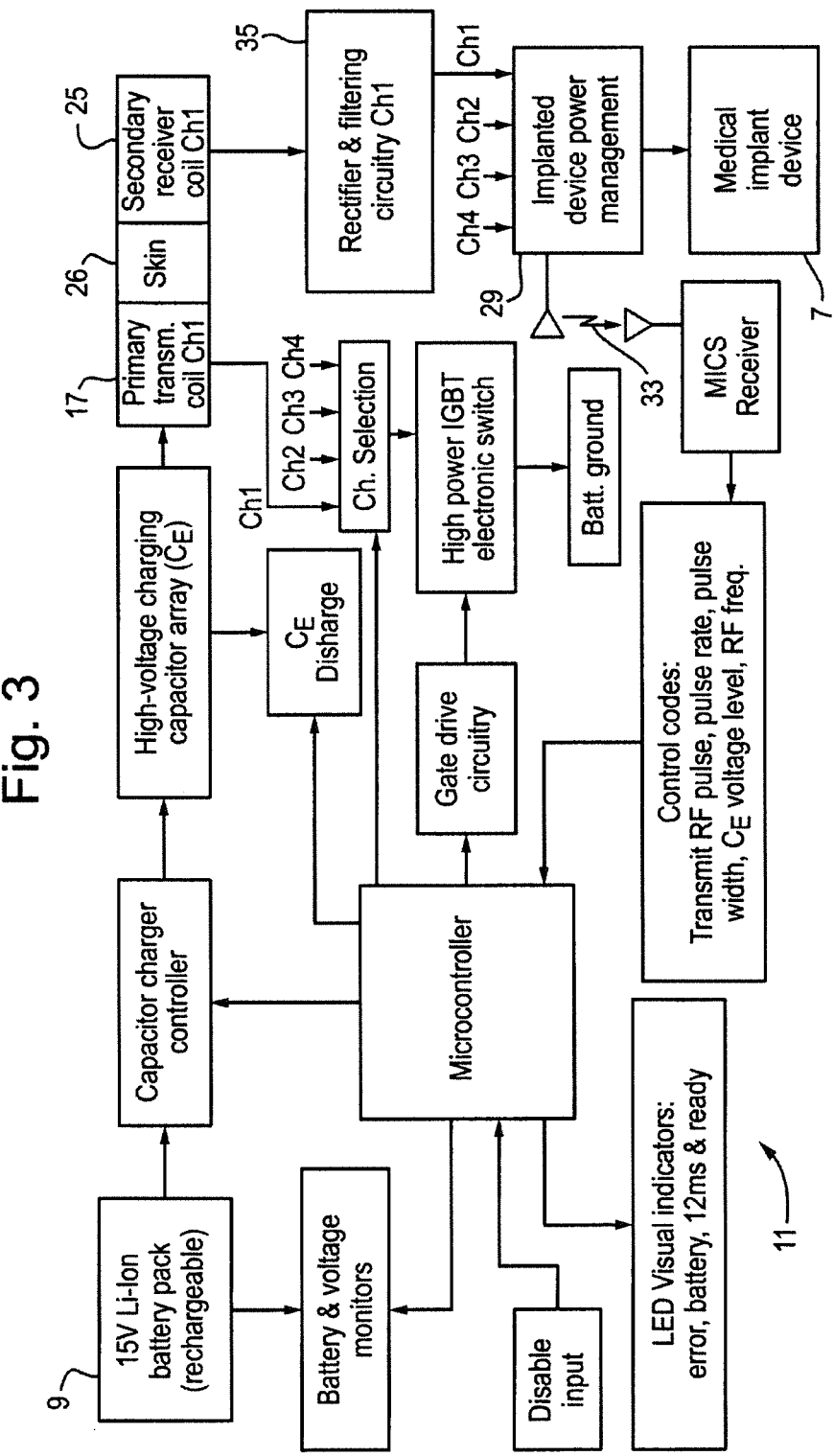
FIG. 3 a block diagram illustrating further details of the basic transmitter system hardware.

FIG. 3 is a block diagram showing further details of the basic transmitter system hardware, in particular the power supply unit 11, e.g. for use in the systems of FIGS. 1 and 2.

As can be seen in FIG. 3, the power supply unit 11 contains a microcontroller for selectively providing pulses across the plurality of channels of the TET system. As shown, a single high energy capacitor, $C_E$, provides voltage to the primary transmitter coils of a plurality of channels. Hence, it is necessary to provide means for selecting which channel power is currently being delivered over. The control of the pulses provided over each channel, and the sequence or order in which the pulses are provided to the plurality of channels is performed by a microcontroller. The microcontroller is operable to select which channel is currently in use, i.e. which channel receives the output from the capacitor $C_E$. The microcontroller is also operable to control the width, rate, voltage and frequency of the pulses provided over the selected channel(s). For example, as shown in FIG. 3, and as mentioned above, voltage pulses may be generated using a switching transistor arrangement, e.g. gate drive circuitry including a high power IGBT electronic switch. By controlling the rate at which the switch is driven, the output of the capacitor $C_E$ may be converted into a series of pulses to be provided over the plurality of channels according to the channel selection component of the microcontroller. The microcontroller may receive as input from the MICS wireless feedback communication link 33 feedback from the power management system 29 of the implantable device 7 to provide control codes indicating e.g. the desired RF pulse widths, pulse rates, discharge voltage level and RF frequency, or desired changes in these responsive to a skin overheating or voltage drop, etc. The microcontroller may also provide the other data relating to the operation of the implanted medical device, the state of the internal rechargeable battery, or data indicative of faults of malfunction mentioned above in relation to FIG. 2 e.g. through LED visual indicators.

Operation of the TET system shown in FIGS. 1, 2 and 3 to deliver energy to the implanted device will now be described.

In use, the power supply unit 11 of the external transmitter apparatus receives power from the external rechargeable battery 9, and uses it to generate a pulsed energy supply over the two channels (Ch1 and Ch2) associated with the respective transmitter coils 17, 19. The energy supplied over each channel is in the form of discrete RF pulses. Each pulse has a RF frequency in the range of 100-300 kHz, e.g. 200 kHz. The RF frequency corresponds to the resonant frequency of the transmitter and receiver coils. The frequency refers to the frequency of the RF signal within each pulse. From 0.03-10 pulses are delivered on each channel per second. Each pulse has a duration i.e. width in the order of milliseconds, such as from 15 ms to 30 ms, typically up to a maximum of 100 ms.

The rate at which pulses are delivered, and the other parameters of the pulses, may be set independently for each channel. Typically the pulses delivered on each channel are of the same frequency and duration. However, whilst the rate at which pulses are delivered may be the same for each channel, the rate at which pulses are delivered may be different for different channels. The rate at which pulses are delivered is variable within a range to allow flexibility to reduce or increase the rate of delivery of pulses on a given channel e.g. to avoid skin overheating as discussed below. Typically therefore, at least for a portion of the operation of the TET system the rate at which pulses are delivered will be different for different channels. Each channel may be allocated a unique time slot within which pulses can be provided over that channel. However, it will be understood that pulses will generally not be provided over each of the channels according to a fixed sequence, but instead the order or sequence in which pulses are provided over the different channels may be varied (or e.g. a particular channel may be temporally disabled), in use, as determined by the power management system 29. Generally, the rate at which pulses are delivered over the plurality of channels should be chosen to maximise the interval between adjacent pulses (across any of the channels) whilst ensuring a continuous supply of power to the implantable device 7. Furthermore, the power supply unit 11 may provide a pulsed power supply over less than all of the channels if appropriate e.g. in the event of a skin overheating situation, as described below. The power supply unit 11 controls the delivery of pulses such that the pulses provided on the two channels do not overlap. Thus, the duration of a pulse on one channel occurs at a time corresponding to an interval between pulses on the other channel. In the example, each pulse delivers 18 J.

Figure 4A:
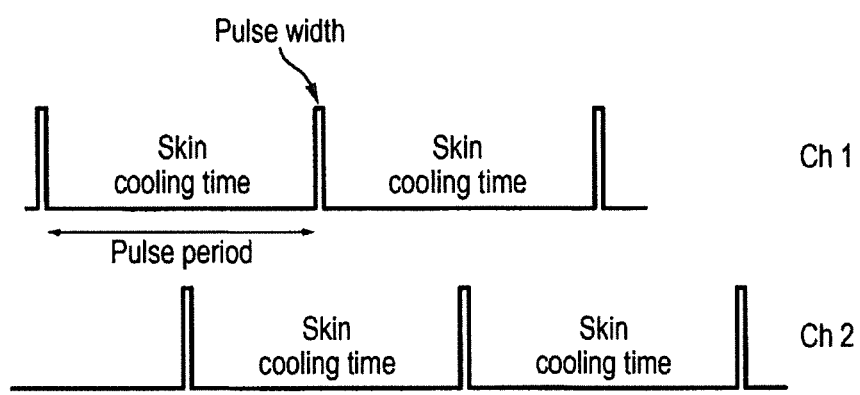
FIGS. 4a and 4b show an exemplary pulse scheme for a two-channel TET system in accordance with embodiments the invention.
Figure 4B:

An exemplary pulse scheme suitable for supplying power to an implantable LVAD device across two channels e.g. using the system described in FIGS. 1-3, is illustrated in FIGS. 4a and 4b. FIG. 4a shows the pulses provided by the power supply unit across first and second channels of the TET system, i.e. to first and second primary coils with respect to time. The pulse widths and pulse periods for each of the two channels should be selected to ensure that sufficient power can be continuously provided to the implantable device. For instance, where a supercapacitor bank is provided in respect of each channel, as shown in FIG. 2, the pulse width and pulse period on each channel should be selected to ensure that the voltage output from each respective supercapacitor bank is sustained above a certain level. For example, FIG. 4b shows how the pulses provided across the first channel act to maintain the supercapacitor voltage output above 14 V. The timing of the pulses across the second channel may be optimised e.g. by maximising the separation between a pulse provided on the first channel and an adjacent pulse provided on the second channel. It has been found that pulse widths of about 15 ms and pulse intervals of around 8 s on each channel are suitable for the two-channel embodiment shown in FIG. 2. That is, these pulse widths and periods allow a continuous supply of power to the implantable device whilst generally allowing sufficient skin cooling. Naturally, other pulse widths, and particularly other pulse intervals, may be required and may be used e.g. depending on the location of the receiver coils on the body and any local overheating of the skin. Furthermore, as discussed elsewhere, the pulse widths, and particularly the pulse intervals, may be dynamically varied in response to feedback provided by the power management system associated with the implantable device.

In embodiments where a single supercapacitor bank common to both channels is provided, the pulse widths and pulse periods on each channel should be chosen to ensure that the supercapacitor is continually charged and maintained above the desired output level. For example, for a two-channel system with both channels charging a common supercapacitor bank, the period between adjacent pulses may be double that shown in FIG. 4a whilst still providing a similar output to that shown in FIG. 4b.

The pulses applied to the transmitter coils 17, 19 result in RF pulses being induced in the receiver coils 25, 27 over the skin interface. Taking channel 1 by way of example, the RF pulses induced in receiver coil 25 pass through the voltage doubler rectifier 35 to be converted to DC pulses, in the example of 8 J. The DC pulses then pass to the supercapacitor bank 39, and act to charge the bank.

Between received pulses, the supercapacitor bank discharges, providing a continuous output voltage with peaks of 14V as illustrated in FIGS. 2 and 4b. This output voltage is provided to the power management system 29. The processing of RF pulses received by the receiver coil 27 over channel 2 is identical, with the pulses being rectified in voltage doubler rectifier 37 before being passed to supercapacitor bank 41, whose output is provided to the power management system 29. It will be appreciated that the supercapacitor banks 39, 41 may be provided within a housing of the power management system 29, or separately therefrom.

The power management system 29 uses the received power to provide a continuous 12 V DC power supply to the implanted device 7, and, where appropriate, provides an energy supply to the internal rechargeable battery 31 to recharge it. It will be appreciated that the internal rechargeable battery 31 may be omitted. However, it is preferably provided as a backup in case the external transmitter apparatus is disconnected, or there is a malfunction of the system. The present invention has been found to reduce reliance on the backup battery in comparison to conventional systems, such that the implanted device can normally be driven without recourse to the battery.

The skin sensors 26, 28 provide data indicative of a sensed internal skin temperature in the region of the receiver coils 25, 27 to the power supply unit 11 of the external transmitter apparatus of the TET system over the wireless feedback link 33. If the sensed skin temperature in the region of one of the receiver coils exceeds a given threshold indicative of a skin overheating situation, the power supply unit 11 either temporarily discontinues the supply of a pulsed energy supply to over the channel associated with that receiver coil, or reduces the rate at which pulses are delivered to the channel as appropriate, to provide the skin with the opportunity to cool down. It will be appreciated that the circulation of blood will typically provide the dominant skin cooling mechanism. The rate at which pulses are delivered to a channel may thus be chosen based on a heart rate or number of heart beats. For example, it has been found that if the skin is sufficiently cooled by about 9 heart beats, then a pulse interval of around 8 seconds is required. If the power supply over one channel is discontinued, or the rate of pulses decreased, the rate of pulses delivered over the remaining channel(s) may be temporarily increased to compensate.

Other data received over the feedback link 33 may be used by the power supply unit 11 in controlling power delivered over the channels, to ensure safe operation and enhanced system reliability. Data indicative of a fault or emergency situation may be transmitted, to allow the power supply unit to discontinue power supply over one or more channels to maintain safe operation. Data may be used to generate an alarm for the user may be transmitted where appropriate. For example, an alarm may be generated to indicate that a transmitter coil is incorrectly positioned and should be repositioned or replaced (e.g. after being removed whilst taking a shower).

In the example described above, it has been found that a 12V, 8 W LVAD may be driven with 8 J pulses at the receiver end, at a rate of 1 pulse/sec. Each supercapacitor bank has a capacitance of 125 mF, and may have a voltage rating of 18V, with a capacitor voltage ripple of 4V i.e. 18V-14V, and a 12V voltage regulator is provided before the LVAD. This may be achieved without needing to provide energy from the internal rechargeable battery 31.

The system and method of the present invention as illustrated in FIGS. 1-4 is advantageous in that the use of the pulsed energy supply over multiple channels enables sufficient power to be supplied to power even higher rated implanted devices e.g. over 2 W, while significantly reducing the risk of the skin overheating in comparison to conventional systems, which use single channel, continuous power delivery. The overheating of the skin is a significant problem, which may lead to long term complications. A further problem arises in relation to being able to recharge an internal backup battery associated with the implanted device in conventional systems. The risk of skin overheating makes it difficult to be able to simultaneously recharge a backup battery and provide power to the device.

As the power supply over each channel is pulsed, there are intervals between pulses in which the skin may cool down, reducing the overall level of heating of the skin. Furthermore, as energy is delivered over multiple channels, the amount of energy that need be delivered over each channel to transfer a particular amount of power to the implantable device and/or backup battery is reduced. This enables sufficient power to power higher rated devices to be more easily transferred, with reduced risk of overheating. Furthermore, the power supply over each channel is independently controllable, such that power delivery over a given channel may be temporarily discontinued, or the rate of pulses delivered decreased, if it is sensed that the skin is becoming too hot in the region of that channel. The rate of pulses delivered over the other channel(s) may then be increased temporarily to compensate. It has been found that it is possible to simultaneously deliver power to recharge an internal backup battery and to drive the implanted medical device without overheating the skin. For example, one channel may be used to deliver power to the backup battery while the other channel delivers power to power the implanted device. In addition, due to the greater power transfer efficiency which may be achieved in accordance with the invention, the need to rely upon the internal backup battery, and hence the need to recharge the battery, may be significantly reduced. As the energy is delivered transcutaneously, the present invention also overcomes problems associated with conventional percutaneous energy transfer systems, which necessitate a driveline being permanently inserted through the skin, leading to problems with infection, and increasing the complexity and invasiveness of installation of the system.

The present invention may be used in conjunction with a range of types of implantable medical device. For example, the device may be an artificial heart pump, such as a ventricular assist device e.g. an LVAD. Alternatively the device may be an artificial heart. The invention may also be used with cardiac defibrillators, atrioverter defibrillators, e.g. passive implantable atrioverter defibrillators (PIAD) devices. Implanted cardiac devices are increasingly used, as rates of heart failure are increasing. Options to treat heart failure are often limited, and transplantation rates are falling due to reduced donor availability. Implanted devices may be used by patients awaiting transplant, or as a longer term treatment. The present invention may be applicable to powering temporarily implanted medical devices e.g. during surgery or electrophysiology study (EPS), for providing atrial defibrillation, ventricular defibrillation, DC cardioversion or resynchronisation of the heart. Of course, the invention is not limited in applicability to cardiac implanted devices, but may be applied to a wide range of other implanted medical devices requiring a power supply. Examples include an artificial urinary bladder, an artificial lung or implanted permanent ventilator, or an artificial kidney. Other applications include drug delivery systems including an implantable device. The implantable device may therefore be an implantable device of a drug delivery system. By way of example, there are a number of cancer treatments involving the use of high power rating implantable devices or electrodes for a sustained period of treatment such as non-thermal irreversible electroporation methods (NTIRE) and continuous low irradiance photodynamic therapy (CLIPT).

The system shown in FIG. 2 uses banks of supercapacitors associated with each channel on the implanted side. While the use of supercapacitors is not essential, it has been found to be particularly advantageous in the context of the pulsed multi-channel power supply used in accordance with the invention. The supercapacitor bank may sustainably deliver power to the power management system for use by the implanted device in a way that reduces the likelihood of having to resort to using the implanted backup battery. This may also provide improved DC to DC energy transfer efficiency. The supercapacitor bank acts in a similar manner to a backup battery, temporarily storing received power. However, while a conventional rechargeable backup battery may be omitted, typically one is still provided to complement the supercapacitor banks.

Internal rechargeable backup batteries, typically being lithium ion (Li-ion) rechargeable batteries, have a limited cycle lifetime of about 400 recharges. Typically, a fully charged implanted lithium ion battery can continuously drive an LVAD only for 20 minutes; about the time required for the patient to shower and get dressed. In comparison to rechargeable batteries, supercapacitors have a much higher power density; (>4000 W/Kg) vs. (<3000/Kg), have a smaller form factor, can be fully charged in milliseconds, and have practically unlimited cycle lifetime. For example, a supercapacitor bank may be only 10% of the weight of a Li-ion battery. However, they have a relatively small energy capacity and consequently need to be frequently recharged. Nonetheless, supercapacitors can be charged virtually instantly (<5 ms). It has been found that the relatively large energy pulses that may be supplied using the multichannel pulsed energy supply approach of the present invention are ideal for providing the required frequent recharging of a supercapacitor bank. The power delivered by a supercapacitor bank can be controlled by the recharging energy pulse rate. Accordingly, the pulsed multichannel approach of the present invention, which may use large pulses due to the reduced likelihood of skin overheating as discussed above, allows the use of supercapacitor banks to be exploited, with the advantages this may provide. It will be appreciated that a conventional single channel continuous transmission TET system would not be readily compatible with the use of a supercapacitor bank. By decreasing reliance upon an implanted rechargeable backup battery, it is expected that the present invention may enable the lifetime of such a battery to be increased from 1-2 years, which is typical with a single channel continuous power supply system, to over 5 years, due to the increased idle time of the battery.

The specification of the supercapacitors forming the supercapacitor bank will depend on the voltage requirements of the implantable device. For the applications described herein such as the LVAD device, it has been found that supercapacitors having a capacitance in the range 10 mF and 5 F and capable of providing a voltage range from 3.5V to 24V may suitably be used. The supercapacitor bank may typically comprise between 1 and 8 capacitors combined appropriately in series and/or parallel to provide the desired equivalent total capacitance and voltage rating. Particularly, it has been found that solid state or electrochemical double layer capacitors, such as the AVX BestCap® capacitors, may be suitable. These provide a high power pulse for a relatively small size (volume) and present an ultra-low equivalent series resistance.

It has been found that the present invention may enable power of up to 25 W to be readily delivered without risk of skin overheating, in comparison to conventional single channel continuous power supply TET systems, which might allow at most 15 W to be provided, with the associated skin overheating risk. As mentioned above, in preferred embodiments a particular construction is used for the receiver coils. The use of such coils has been found to be advantageous in its own right, and such coils may be used in the context of other implantable systems requiring one or more receiver coil for receiving a transmission, e.g. signal transcutaneously from an external transmitter coil. For example, a receiver coil of this construction may be used in an implantable apparatus of a defibrillator device, to receive an RF pulse transmitted by an external transmitter apparatus of the device.

Figure 5:
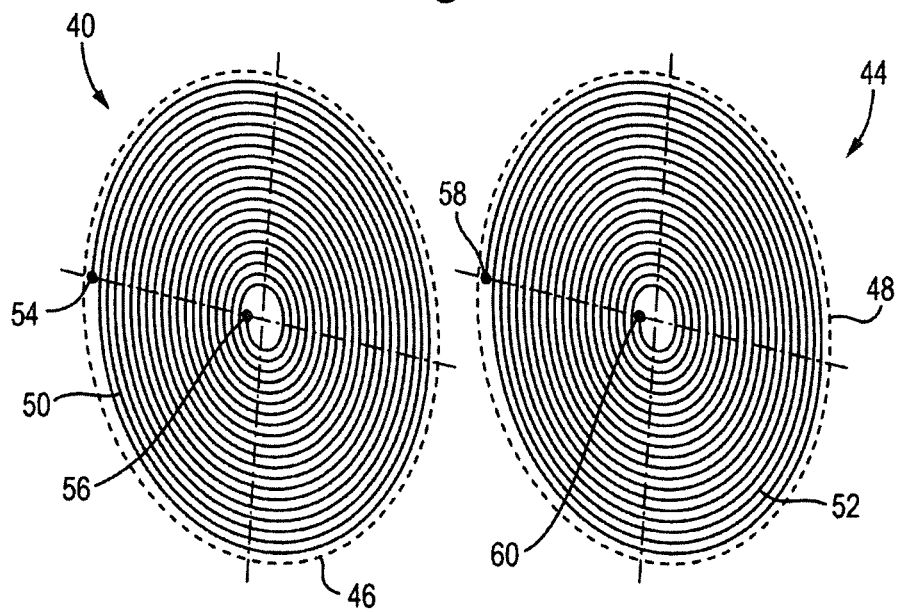
FIG. 5 is an exploded plan view of one of a pair of coil sub-assemblies used to provide a flexible receiver coil in accordance with an embodiment of the invention.

FIG. 5 is an exploded plan view of one of a pair of coil sub-assemblies 40 used to provide a flexible receiver coil in accordance with a preferred embodiment of the invention. It will be appreciated that the construction illustrated in FIG. 5 (and the following figures) may alternatively or additionally be used to provide a flexible transmitter coil in accordance with further aspects or embodiments of the invention. The coil sub-assembly 40 includes two coil layers 42, 44. Each coil layer is defined by an oval disc shaped piece of a flexible polyimide substrate 46, 48 respectively, having a spiral coil portion 50, 52 printed on one side thereof. The rounded edges of the substrate pieces help to provide increased comfort and biocompatibility with the wearer. Each piece of substrate 46, 48 has a maximum diameter in the range of from 40-50 mm. Each coil portion includes two terminals, terminals 54, 56, 58 and 60 respectively. The coil portions 50, 52 are defined by a pattern of a metallic conductive material, and preferably from gold, platinum, silver, or an associated alloy. These metals are preferred because of their low resistivity (15.9 nΩ·m) and biocompatibility. The conductive material may be printed on to the substrate using photolithography, ink-jet printing, or laser milling. Rather than using flexible polyimide as the substrate, coil portions may be printed onto a flexible silicone or PTFE substrate. The polyimide flexible material is preferred due to its high thermal stability (~400° C.), electrical isolation, flexibility and biocompatibility. Flexible substrates are used because they allow the resultant coil to be comfortably bent around the subcutaneous chest wall. Biocompatibility, which includes the mechanical and chemical leaching of the materials, is an important consideration in this field. A coil may be manufactured to provide a high degree of biocompatibility by limiting the residual and bulk chemistry of the metals, substrates and chemicals used in processing to try to avoid any leaching, thus avoiding sensitivity or cytoxicity issues.

In some exemplary arrangements the metallic conductor material can be deposited in the form of a thin film (of from about 5 μm to 30 μm thickness) deposited via RF sputtering, thermal evaporation, e-beam deposition or ion beam techniques. With these processes a deposited seed layer (e.g. 2 nm to 10 nm of Titanium) can be used to enhance adhesion. Such thin films will allow ultra-fine patterning (down to 100 nm track widths if required), and will be highly conductive due to their thin film nature. For example, no binder need be used, and the films will have a fine microstructure. Patterning for such films will involve photo-resist based photolithography techniques, 3D laser milling or shadow masking during deposition. The choice of technique will depend on the track widths and quality that are required. Use of an ink containing powder is another possible method of forming the coil portions, and may provide the advantage of a low cost set-up and ease of manufacture. These thick film techniques are suitable for printing at room temperature and it has been found that the films provide a good conductivity after sintering/baking at between 100 degrees C. to 300 degrees C. The powder may be deposited in a desired pattern, and then subjected to sintering/baking to fix the deposited material. The sintering/baking temperature has an influence on the resistivity. The higher the temperature, which in practice will be limited by substrate/frit and thermoplastic, the shorter the sintering time needed to reach a certain conductivity (e.g. 5-30 μΩ·cm).

However they are produced, the two coil layers 42, 44, are adhered to one another with the printed coil portions 50, 52 to the interior of the resulting laminate. This means that the printed coil portions are isolated from the external environment by the reverse side of the substrates on which they are printed. The coil layers are adhered only at the outer periphery thereof and at the geometric centre, to maintain flexibility of the resulting coil sub-assembly. The coil portions 50, 52 make metal contact on the inside of the laminate. This process to fabricate a coil increases the effective cross-section of the printed metallic conductor.

Figure 6:
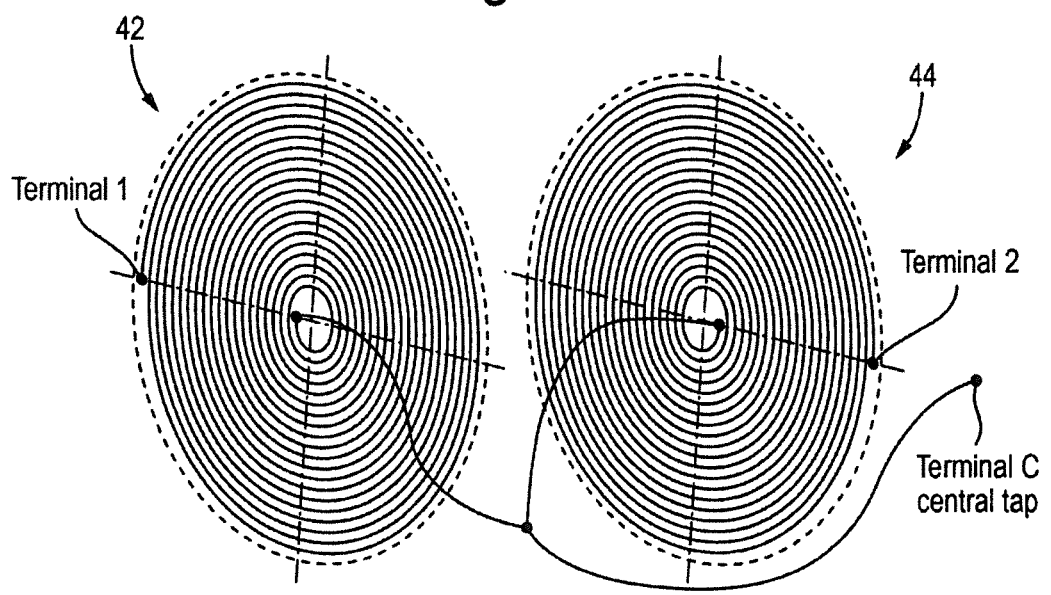
FIG. 6 shows how two coil sub-assemblies may be connected in series.

In order to construct a coil, two coil sub-assemblies 50, 52, each formed as described in relation to the coil sub-assembly 40 of FIG. 5, and having N turns, are connected in series in the manner shown in FIG. 6. The coil sub-assemblies are adhered to one another face to face at their periphery and at the centre, as described in relation to joining the coil layers that define each coil sub-assembly. The resulting receiver coil is therefore formed from four coil layers. Of course, a coil may alternatively be defined by only a single coil sub-assembly of the type obtained as described in relation to FIG. 5, and will then have 2 coil layers. Coils having any number of coil layers are envisaged depending upon the requirements for the coil e.g. effective coil cross section. As will be described below, tuning capacitors may be associated with each coil sub-assembly to tune the coil to the resonant frequency of the transmitter coil it is to couple with.

As schematically illustrated in FIG. 6, the coil sub-assemblies 50, 52 are connected in series at the central tap point C. Three output terminals, the tap terminal C, and terminals 1 and 2 are defined from the resulting coil assembly. This arrangement of output terminals is exemplary, and has been found to be advantageous in connecting the receiver coil to a power delivery lead, which is used in accordance with some preferred embodiments of the invention. Such a lead would be omitted where the coils are used to provide transmitter coils, but the construction of the coils may otherwise be identical.

Figure 7A:
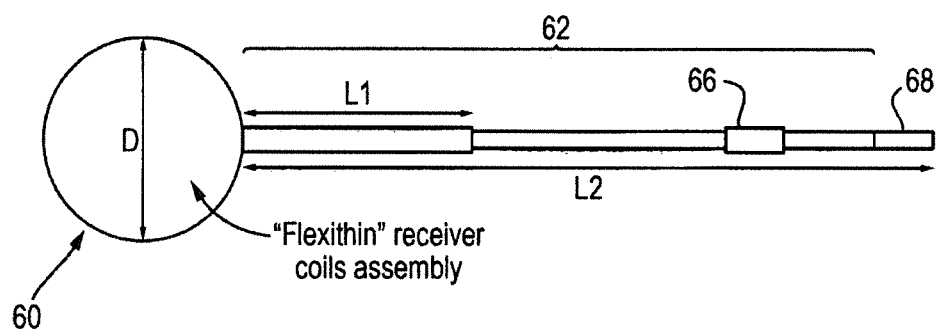
FIG. 7a is a top plan view of a receiver coil obtained in accordance with the process described by reference to FIGS. 5 and 6, with the coil being connected to a flexible lead.
Figure 7B:
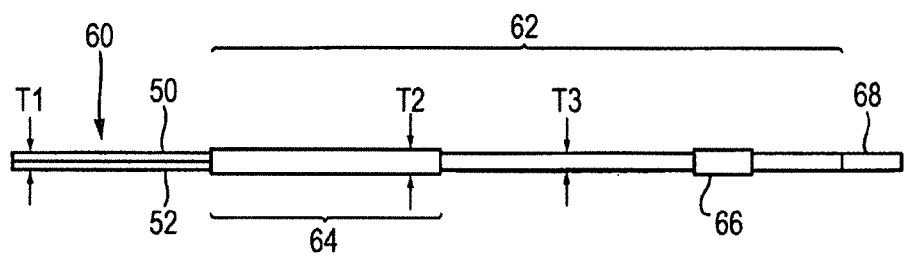

FIG. 7a is a top plan view of a receiver coil 60 obtained in accordance with the process described by reference to FIGS. 5 and 6, with the coil being connected to a flexible lead, and FIG. 7b is a longitudinal cross sectional view through the coil and flexible lead of FIG. 7a along the line b-b. The receiver coil 60 and flexible lead shown in FIGS. 7a and 7b is designed for use in a defibrillator application.

Figure 14:
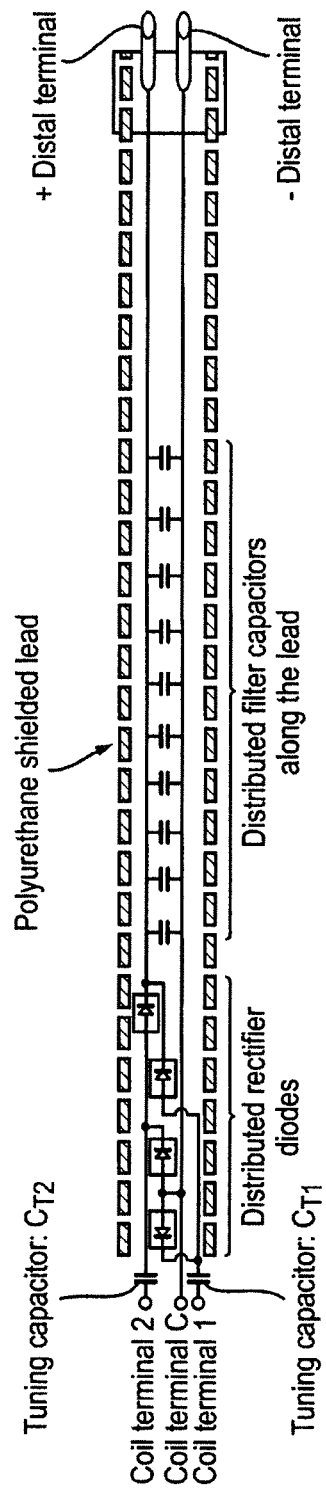
FIG. 14 illustrates another flexible lead construction.

Referring to FIGS. 7a and 7b, the receiver coil 60 corresponds to the receiver coil obtained when the coil sub-assemblies 50, 52 are connected to one another. The upper and lower coil sub-assemblies 50, 52 are schematically illustrated in FIG. 7b. The coil 60 is a flexible disc of an elliptical shape, having a minimum diameter in the range of from 40-50 mm. The coil has a thickness T1 in the range of from 0.2-1.5 mm. The receiver coil 60 is connected to a flexible lead 62 at the proximal end of the lead. The lead 62 has a first section 64, of relatively greater thickness T2 e.g. 2 mm, adjacent to the coil 60. The remainder of the flexible lead is of lesser thickness T3 e.g. 1.5 mm. At the distal end of the flexible lead a pair of spaced electrodes 66, 68 are provided. Alternatively suitable output terminals may be used in place of the electrodes, as shown in FIG. 14, depending upon the application of the lead.

The lead 62 is flexible, and integrates components for rectifying the output of the coil, and filtering the resulting rectified signal. The components for rectifying the output of the coil comprise a plurality of diodes embedded in the thicker proximal section 64. This section has a length L1 which may be 60 mm. The lead 62 as a whole has a length L2, which may be in the range of from 25-70 cm to fit the body of a user (ranging from an infant to large adult). The thinner portion of the lead distal to the proximal section 64 may be provided by a section of coaxial cable, which provides passive filtering functionality, or may comprise a set of filter capacitors distributed along its length.

Figure 8A:
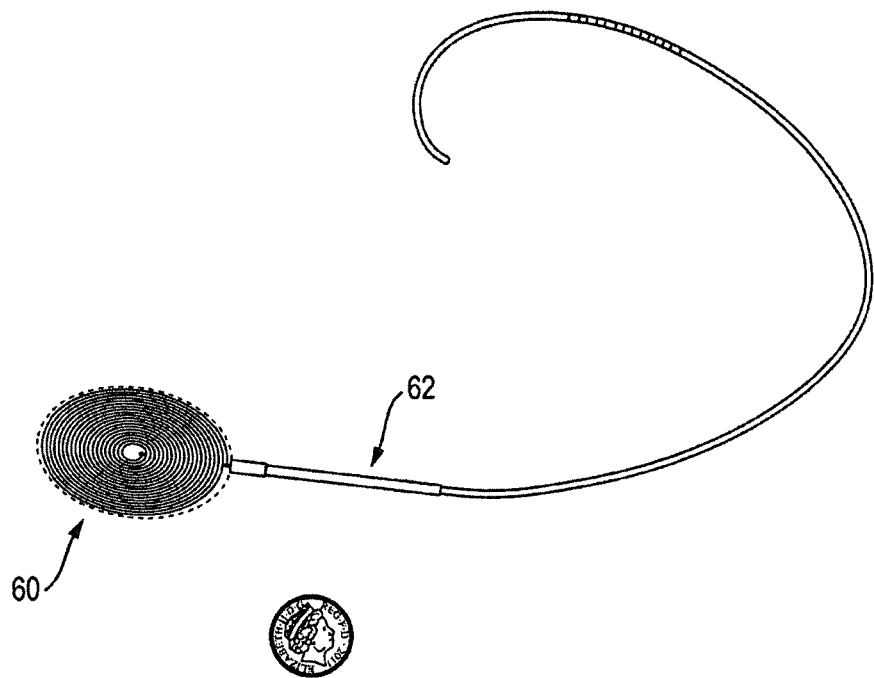
FIGS. 8a and 8b show a prototype 3D model of a receiver coil and its flexible lead.
Figure 8B:
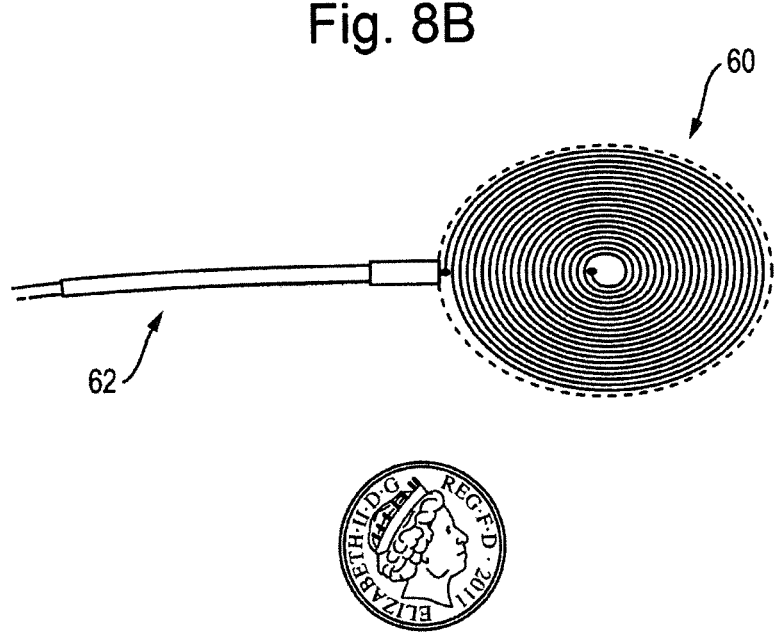

FIGS. 8a and 8b are views of a prototype 3D model of a receiver coil 60 and its flexible lead 62 of the type shown in FIGS. 7a and 7b, with a coin to illustrate scale.

The flexible lead may be provided using materials used in conventional transvenous catheters e.g. medical graded silicone and polyurethane. The lead may have a polyurethane outer sheath. Generally, the lead, or at least the outer isolation material of the lead should be fully biocompatible, light and flexible. The lead should also be durable and reliable, as it may potentially be implanted for an extended period of time (i.e. years). The properties of the material(s) used for the lead may be selected as required, depending upon the demands expected to be placed on the lead in use.

It will be appreciated that the flexible receiver coil construction of the present invention as described by reference to FIGS. 5 to 7b is advantageous in the context of the TET system of the earlier aspects of the invention. Each one of the receiver coils 17, 19 of FIGS. 1 and 2 may be provided by such a flexible coil, with or without the attached flexible lead. In preferred embodiments the lead is used, and provides a power delivery lead. The rectifier circuitry e.g. 35 shown in FIG. 2 may be provided by a rectifier section of the lead as shown in FIGS. 7a and 7b. The distal end of the lead may be connected via suitable terminals to an input of the supercapacitor bank e.g. 39 associated with the coil, or alternatively to an input of the power management system 29 if appropriate. In these applications the electrodes 66, 68 may be replaced by output terminals as shown in FIG. 14. Similarly, the transmitter coils of FIGS. 1 and 2 may alternatively or additionally be provided by the coils shown in FIGS. 5-7b, though without the flexible lead.

Nonetheless, the receiver coil construction is also advantageous to provide an implantable receiver coil in other contexts. For example, the coil may be used as a receiver coil of an implantable apparatus of a cardiac defibrillator apparatus. The coil may receive an RF pulse transmitted from a transmitter coil of an external transmitter apparatus of the defibrillator apparatus, for use in delivering a defibrillating pulse to a heart. In these embodiments, the coil is advantageously attached to a flexible lead as shown in FIGS. 7a and 7b terminating in electrodes 66, 68. The electrodes may be implanted in the heart, with the rectifying and filtering provided by the flexible lead appropriately processing a received RF pulse to provide a DC pulse suitable for application to the heart. In other applications, the receiver coil may be used in a receiver apparatus of an implantable apparatus for delivering a pulse to the brain or another body part, with the electrodes then being implanted in the appropriate body part in use. The coils may also be used as transmitter coils in other contexts, such as those mentioned above in relation to the receiver coils.

The construction of a flexible lead 62 of the type shown in FIGS. 7a and 7b, and its connection to the receiver coil will be described by reference to FIG. 9.

As mentioned above, this construction would be particularly suitable for the defibrillator application. Power delivery applications may utilize a relatively simple lead comprising a pair of wires (without electrodes at the distal ends thereof).

Figure 9:
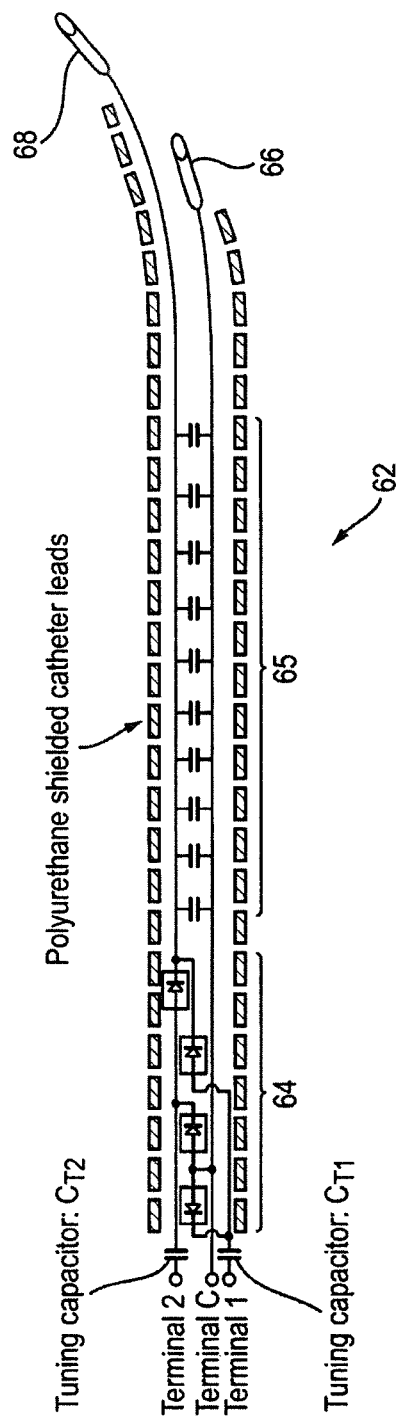
FIG. 9 shows a flexible lead construction.

The three terminals out of the receiver coil shown in FIG. 6 i.e. terminals 1, C and 2, are connected to corresponding input terminals at the proximal end of the lead as shown in FIG. 9. Tuning capacitors are provided for tuning each coil sub-assembly 50, 52 to the resonant frequency of the transmitter coil i.e. the frequency of the RF pulses to be applied. The values of the tuning capacitors $C_{T1}$ and $C_{T2}$ will also depend on the number of turns (N) in the coils present in each coil sub-assembly. Typical values of 10 nF would be appropriate for N=30, and where the resonant frequency $f_o$=240 kHz.

As shown in FIGS. 7a and 7b, the lead includes a set of diodes distributed along its length at the proximal end in portion 64, providing rectifier functionality. Suitable microelectronic diodes for the embedded rectifier have been found to be: MUR5480ET36 or STTH310S. A set of filter capacitors is distributed along the length of the section 65 of the lead. In some exemplary embodiments it has been found that the total value of the parallel filter capacitors should be at least 470 nF, for good ripple filtering performance. Thus, about 10 microelectronics capacitor elements of 47 nF, 250 V, could be used. The electrodes 66, 68 may be provided using any suitable material. For example, where the coil and the catheter lead are intended to be used in an implantable apparatus of a defibrillator device, the electrodes may be made of any material suitable for use in this context. A transient voltage suppressor (TVS) device may optionally be embedded in parallel with the distributed filtering capacitors e.g. SM15T200CA, for 200V. This will help to protect the device against an overvoltage, e.g. if the electrodes are not suitably connected e.g. to a heart.

Figure 10A:
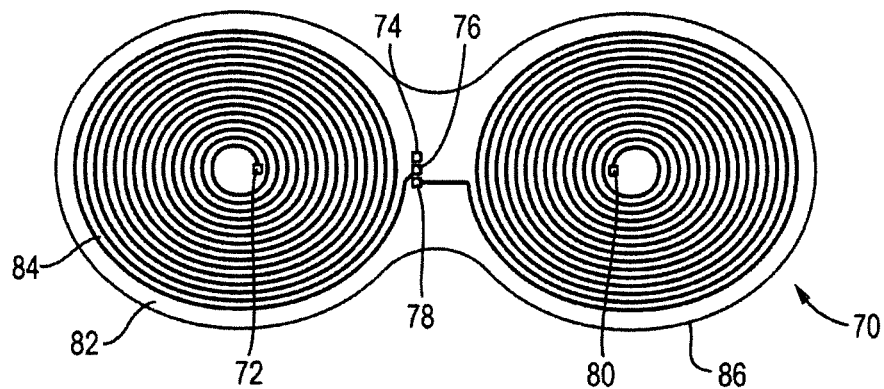
FIGS. 10a-c illustrate another flexible coil construction.

An alternative receiver (or transmitter) coil construction will be described by reference to FIG. 10a. FIG. 10a illustrates the top layer 70 used in providing the coil. The top layer is defined by a piece of a flexible substrate 82 e.g. polyimide, having two spiral coil portions 84, 86 (each comprising 15 turns) printed side by side on one surface thereof. The coil portions have terminals 72, 74, 76, 78, 80. Both coil portions are therefore printed on the same piece of substrate. The techniques and materials used in providing the printed coil portions, and the flexible substrate, may be as described in relation to the earlier embodiment of FIG. 6.

Figure 10B:
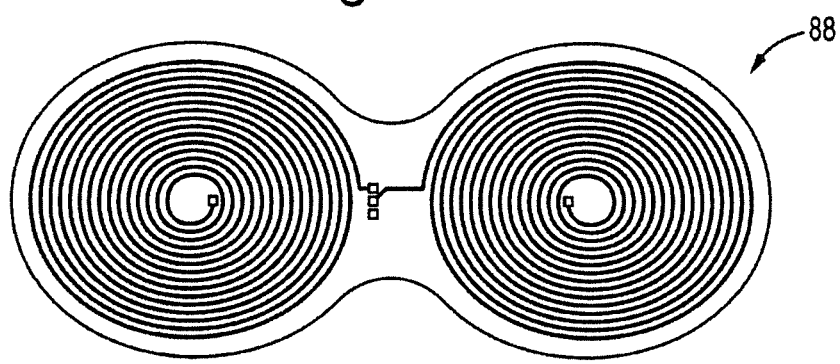

FIG. 10*b* illustrates a bottom layer 88 used in providing the coil. This is of similar construction to the top layer, with the only differences being in relation to the connections between the coil portions and the various terminals.

Figure 10C:
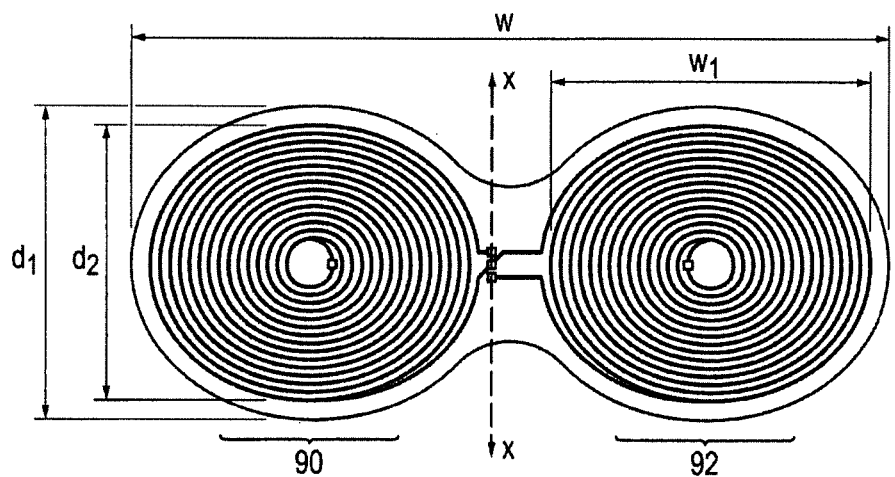

The top and bottom layers are adhered to one another with the coil portions to the interior of the resulting laminate, again, only at the periphery and centre of the coil portions. The resulting structure provides a 60-turn coil as shown in FIG. 10*c* with a central tap terminal provided between a 30-turn coil formed between the left side top and bottom layer coil portions and a 30-turn coil formed between the right side top and bottom layer coil portions. This structure defines two coil sub-assemblies 90, 92, similar to those shown in FIG. 6, but being connected by a common substrate layer. The structure may be folded in half in the direction of the arrow along the line X-X in FIG. 10*c*, and the sub-assemblies adhered to one another at the periphery and centre to provide a receiver coil including four coil layers, similar to that obtained in FIG. 6. One exemplary set of approximate dimensions for the FIG. 10*c* construction is as follows; d1=63 mm, d2=53 mm, w=152 mm w1=65 mm. The thickness of the tracks defining the spirals of each coil may be 1 mm.

The resulting coil construction may be connected to a flexible lead in the same manner as the coil 60 of FIG. 7*a*, 7*b* and 9 or 14, and is suitable for use in the various possible applications e.g. in the power delivery or defibrillator applications. A receiver coil described by reference to FIGS. 5 to 10 may be used with any conventional transmitter coil, and may be tuned to any desired transmitter coil. The receiver coil may be customised to different body sizes. It is envisaged that the coil may provide benefits in many contexts where an implanted receiver coil is required, through improved coupling to a transmitter coil, and improved conformability to a user. Similar benefits arise when the coil is used as a transmitter coil, with similar or conventional receiver coils. The application is not limited to the defibrillator and power delivery contexts.

Returning to the TET system of FIGS. 1 and 2, when this is used in combination with the flexible receiver coil construction described by reference to FIGS. 5 to 10, further advantages are obtained. A high level of DC to DC energy transmission efficiency may be obtained, which has been found to be more than twice that of conventional single channel continuous TETS. For example, an efficiency of 65% has been obtained over a 12 mm skin thickness, in contrast to 25% using conventional systems. The use of the flexible thin receiver coils may provide a larger stable coupling area and transmission efficiency, efficient power control, and minimal movement and decoupling, as the weight of the coils may be minimised. This may help further increase the lifetime of an internal rechargeable battery.

FIG. 11 illustrates the results of preliminary bench test evaluation of the DC to DC energy transfer obtained using a TET system in accordance with FIGS. 1 and 2. FIG. 11 shows the transmission efficiency measured against inter-coil air gap, for an external capacitor Ce (representing the energy storage means of the power supply unit) voltage setting at 50V (square points), and 100V (diamond points), and with a pre-charged (2 shot=25V) capacitive load of 600 µF (to replicate a dummy low value supercapacitor bank load) at the secondary side. The efficiency was found to peak at the 15 mm gap at about 80%. If used with a resistive load (if power is directly delivered to a DC motor), the efficiency is only of 55% with that gap distance.

Table 1 illustrates the efficiency of the system at various pre-charge value of capacitive load.

| Voltage | Efficiency |
| --- | --- |
| 0.3 | 1.45 |
| 5 | 25.56 |
| 10 | 40.84 |
| 15 | 49 |
| 20 | 58.39 |
| 25 | 76.6 |
| 30 | 76.8 |
| 35 | 76.1 |
| 40 | 75.3 |

Figure 12:
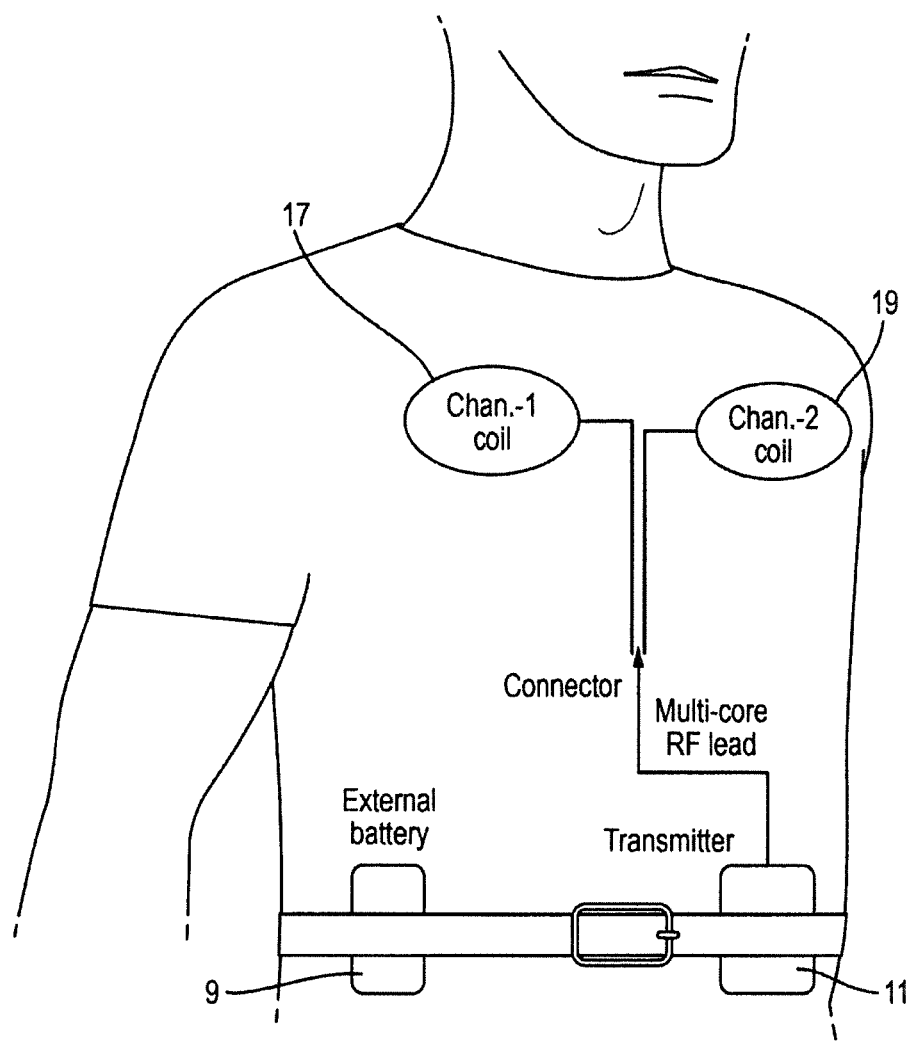
FIG. 12 illustrates a TET system disposed in an "in use" configuration with respect to a user in accordance with another embodiment of the invention.
Figure 13:
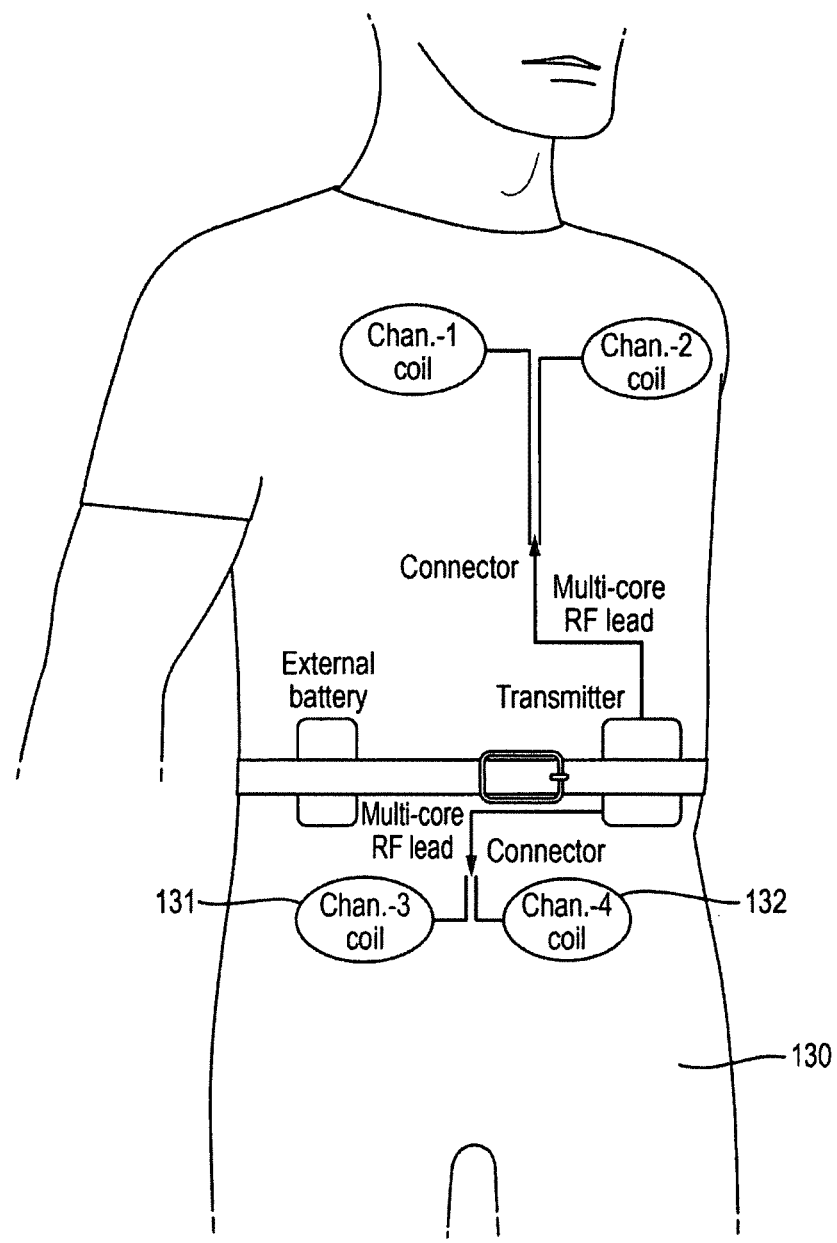
FIG. 13 illustrates a TET system disposed in an "in use" configuration with respect to a user in accordance with yet another embodiment of the invention.

FIGS. 12 and 13 show two further embodiments of the invention, where instead of the transmitter coils being directly mountable to the torso of a user, the transmitter coils are provided as part of a wearable garment or garments. The coils are thus held in place on the wearer's body by the garment(s). The garment(s) may be disposable i.e. not intended to be washed and may be worn over a user's normal underwear (but beneath their other clothing). The coils may be arranged to be releaseably connectable to the remainder of the external power transmitter apparatus, i.e. the power supply unit 11 and external battery 9. In this way the coil unit comprising the garment and its transmitter coils can be replaced when worn out or dirty, or with a different coil unit, without requiring replacement of the whole external power transmitter apparatus.

In the FIG. 12 embodiment, the external battery 9 and power supply unit 11 are provided on a belt, similarly to FIG. 1, but the first and second transmitter coils 17, 19 are now mounted on a vest to be worn by the user. The coils 17, 19 are thus held in position on the chest wall of the wearer.

In the FIG. 13 embodiment, two further transmitter coils 131 and 132 are provided on a pair of shorts and are thus held in position on the abdomen of the wearer. FIG. 13 thus relates to a four-channel system.

It will be appreciated that transmitter coils may generally be mounted on any other suitable garments and held in position at any suitable anatomical position on the wearer. It will also be appreciated that the use of the flexible transmitter coils described above, whether or not used in the context of a TET system, is particularly compatible with these embodiments where the transmitter coils are provided as part of a garment to be worn by the user.

The invention claimed is:

1. An external transmitter apparatus for a transcutaneous energy transfer (TET) system for supplying power for use in energising an implantable medical device in use, the external transmitter apparatus comprising;

a plurality of transmitter coils, each transmitter coil being configured to transmit power transcutaneously to a respective one of a plurality of receiver coils of an implantable receiver apparatus of the TET system when located in proximity thereto in use for use in energising an implantable medical device connected to the implantable receiver apparatus in use, the external transmitter apparatus of the TET system further comprising a power supply unit for providing a pulsed power supply to each one of the transmitter coils of the external transmitter apparatus in use for transmission transcutaneously by the transmitter coil to a respective receiver coil of the implantable receiver apparatus located in proximity thereto, wherein each transmitter coil is associated with a respective power supply channel of a plurality of power supply channels of the external transmitter apparatus, and the power supply unit is arranged to deliver the pulsed power supply to each transmitter coil of the external transmitter apparatus over the respective power supply channel associated therewith and wherein the power supply unit comprises a microcontroller for controlling the supply of power over the different power supply channels of the external transmitter apparatus, the microcontroller being configured to control a timing of pulses of the pulsed power supply provided on different ones of the plurality of power supply channels such that each power supply channel has a different respective timeslot in which the pulses are provided over that power supply channel.

2. The apparatus of claim 1 wherein the external transmitter apparatus has from 2 to 4 transmitter coils.

3. The apparatus of claim 1 wherein the microcontroller is arranged to control a timing of the pulses of the pulsed power supply provided on each of the different power supply channels such that there is no overlap in time between pulses provided on any ones of the different power supply channels.

4. The apparatus of claim 1 wherein the microcontroller is arranged to control the supply of power on the plurality of power supply channels based at least in part upon received data relating to the temperature of the skin of the user, wherein the temperature of the skin of the user is indicative of an internal skin temperature of the user in the vicinity of each transmitter-receiver coil pair.

5. The apparatus of claim 4 wherein the microcontroller is arranged to temporarily cease power supply over a power supply channel associated with a transmitter coil where the temperature of the skin in the vicinity of the transmitter-receiver coil pair of which the transmitter coil forms part exceeds a threshold temperature or wherein the microcontroller of the external apparatus is arranged to vary a rate of the energy pulses delivered over a power supply channel to the respective transmitter coil associated therewith based on received data indicative of a temperature of the skin in the region of the transmitter-coil pair of which the transmitter coil forms part.

6. The apparatus of claim 1 wherein the power supply unit is arranged to deliver a pulsed power supply over each power supply channel in which the duration of each pulse is in the range of from 10 ms to 100 ms.

7. The apparatus of claim 1 wherein the power supply unit is arranged to deliver a pulsed power supply over each power supply channel in which the interval between consecutive pulses on each power supply channel is in the range of from 100 ms to 30 s.

8. The apparatus of claim 1, wherein the transmitter coils are provided on one or more wearable garments.

9. The apparatus of claim 1 wherein each of the transmitter coils of the external transmitter apparatus is a flexible spiral coil comprising at least one coil layer, comprising a coil portion printed on a layer of a flexible substrate.

10. A transcutaneous energy transfer (TET) system for supplying power for use in energising an implantable medical device in use, the TET system comprising;
an external transmitter apparatus and an implantable receiver apparatus, wherein the implantable receiver apparatus is connected or connectable to an implantable medical device for supplying power thereto in use;
the external transmitter apparatus comprising a plurality of transmitter coils, each transmitter coil being configured to transmit power transcutaneously to a respective one of a plurality of receiver coils of the implantable receiver apparatus when located in proximity thereto in use for use in energising an implantable medical device connected to the implantable receiver apparatus in use,
the external transmitter apparatus of the TET system further comprising power supply unit for providing a pulsed power supply to each one of the transmitter coils of the external transmitter apparatus in use for transmission transcutaneously by the transmitter coil to a respective receiver coil of the implantable receiver apparatus when located in proximity thereto, and wherein each transmitter coil is associated with a respective power supply channel of a plurality of power supply channels of the external transmitter apparatus, and the power supply unit is arranged to be able to deliver the pulsed power supply to the transmitter coil of the external transmitter apparatus over the respective power supply channel associated therewith and wherein the power supply unit of the external transmitter apparatus comprises a microcontroller for controlling the supply of power to the transmitter coils over the different power supply channels of the external transmitter apparatus, wherein the microcontroller is configured to control a timing of the pulses of the pulsed power supply provided on different ones of the plurality of power supply channels such that each power supply channel has a different respective timeslot in which pulses are provided over that power supply channel.

11. The system of claim 10, wherein the microcontroller is arranged to control the supply of power on the plurality of power supply channels based at least in part upon received data relating to the temperature of the skin of the user.

12. The system of claim 10 wherein the implantable receiver apparatus comprises a power management system, and is arranged such that power received by each receiver coil from a transmitter coil of the external transmitter apparatus is delivered to the power management system wherein the power management system of the implantable receiver apparatus of the TET system is arranged to transmit data to the external apparatus of the TET system relating to the temperature of the skin of the user for use by the external transmitter apparatus in controlling the supply of power to the transmitter coils over the plurality of power supply channels.

13. The system of claim 10 wherein the implantable receiver apparatus of the TET system comprises a rectifier for rectifying the pulsed power supply received by each receiver coil from a transmitter coil of the external apparatus, wherein the rectifier is provided in respect of each receiver coil.

14. The system of claim 10 wherein the implantable receiver apparatus of the TET system is connected to a rechargeable backup battery for the implantable medical device, and the power management system is arranged to selectively provide received power to the implantable medical device and/or to the rechargeable backup battery; and/or wherein power received from one of the receiver coils is dedicated to recharging the backup battery.

15. The system of claim 10 wherein the implantable receiver apparatus comprises a converter for converting each pulsed energy supply received from the receiver coils to a continuous power supply for use in energising the implantable medical device.

16. The system of claim 10 wherein the implantable receiver apparatus is arranged such that power received by each receiver coil is delivered to a capacitor arrangement for temporary storage prior to being provided to the power management system, wherein a single capacitor arrangement is provided for all the receiver coils.

17. The system of claim 10, wherein at least one receiver coil of the plural receiver coils of the implantable receiver apparatus is a flexible receiver coil, and wherein the flexible receiver coil comprises at least one coil layer comprising a coil portion, and wherein the coil portion is printed on a flexible substrate.

18. An implantable receiver apparatus connected to an implantable medical device,
wherein the implantable receiver apparatus is an implantable receiver apparatus of a cardiac defibrillator apparatus, wherein the implantable receiver apparatus is arranged to receive a RF pulse transmitted transcutaneously by an external transmitter apparatus of the cardiac defibrillator apparatus in use and to use the received RF pulse in applying a defibrillating pulse to implantable electrodes connected to the implantable receiver apparatus to enable a defibrillating pulse to be delivered to a heart when the electrodes are implanted in a heart in use,
the implantable receiver apparatus comprising one or more flexible receiver coils or capacitor plates, each flexible receiver coil or capacitor plate being arranged to receive a transmission from a complimentary capacitor plate or coil of the external transmitter apparatus when in proximity thereto in use, wherein each of the receiver coils or capacitor plates of the implantable apparatus comprises at least one coil layer or capacitor plate comprising a coil portion or a thin metal layer portion, wherein the coil portion is printed on a flexible substrate or the thin metal layer portion is printed on a flexible substrate.

19. The apparatus of claim 18 wherein each flexible coil or capacitor plate of the implantable receiver apparatus is connected to a proximal end of a respective flexible power delivery lead for transporting a received transmission away from the coil or capacitor plate, wherein one or both of a filter or converter for the coil or capacitor plate are associated with the respective flexible power delivery lead, wherein the components of each of the filters or converters are distributed along the length of the respective flexible power delivery lead.

20. An external transmitter apparatus for a transcutaneous energy transfer (TET) system for supplying power for use in energising an implantable medical device in use, the external transmitter apparatus comprising;
a plurality of external transmitters, each external transmitter being configured to transmit power transcutaneously to a respective one of a plurality of implantable receivers of an implantable receiver apparatus of the TET system when located in proximity thereto and further configured to energise an implantable medical device connected to the implantable receiver apparatus in use,
the external transmitter apparatus of the TET system further comprising a power supply unit for providing a pulsed power supply to each one of the external transmitters of the external transmitter apparatus in use for transmission transcutaneously by the external transmitter to a respective implantable receiver of the implantable receiver apparatus located in proximity thereto, wherein each external transmitter is associated with a respective power supply channel of a plurality of power supply channels of the external transmitter apparatus, and the power supply unit is arranged to deliver the pulsed power supply to each external transmitter over the respective power supply channel associated therewith and wherein the power supply unit comprises a microcontroller for controlling the supply of power over the different power supply channels of the external transmitter apparatus, the microcontroller being configured to control a timing of pulses of the pulsed power supply provided on different ones of the plurality of power supply channels such that each power supply channel has a different respective timeslot in which the pulses are provided over that power supply channel.

21. The apparatus of claim 20, wherein the pulses are radio frequency pulses, the power supply channels are wireless and the microcontroller is configured to control the duration of pulses.

* * * * *